United States Patent
Meulewaeter et al.

(10) Patent No.: US 12,325,861 B2
(45) Date of Patent: Jun. 10, 2025

(54) REGULATORY NUCLEIC ACID MOLECULES FOR ENHANCING GENE EXPRESSION IN PLANTS

(71) Applicant: BASF SE, Ludwigshafen (DE)

(72) Inventors: Frank Meulewaeter, Ghent (BE); Christophe Liseron-Monfils, Ghent (BE)

(73) Assignee: BASF SE, Ludwigshafen am Rhein (DE)

( * ) Notice: Subject to any disclaimer, the term of this patent is extended or adjusted under 35 U.S.C. 154(b) by 168 days.

(21) Appl. No.: 17/781,904

(22) PCT Filed: Nov. 30, 2020

(86) PCT No.: PCT/EP2020/083879
§ 371 (c)(1),
(2) Date: Jun. 2, 2022

(87) PCT Pub. No.: WO2021/110582
PCT Pub. Date: Jun. 10, 2021

(65) Prior Publication Data
US 2023/0148071 A1    May 11, 2023

(30) Foreign Application Priority Data

Dec. 3, 2019 (EP) .................................. 19213158

(51) Int. Cl.
*C12N 15/82* (2006.01)
*C12N 15/10* (2006.01)

(52) U.S. Cl.
CPC ..... *C12N 15/8216* (2013.01); *C12N 15/1065* (2013.01); *C12N 15/1072* (2013.01); *C12N 15/8213* (2013.01)

(58) Field of Classification Search
None
See application file for complete search history.

(56) References Cited

U.S. PATENT DOCUMENTS

2012/0167248 A1*  6/2012  Kuhn et al. ........ C12N 15/8216
800/287

FOREIGN PATENT DOCUMENTS

| JP | 2007259751 A | * 10/2007 |
|---|---|---|
| WO | WO-2011/023537 A1 | 3/2011 |
| WO | WO-2018/113702 A1 | 6/2018 |
| WO | WO-2020/229241 A1 | 11/2020 |

OTHER PUBLICATIONS

Huang et al., (2008), GenBank: EU189088, Triticum aestivum LMW-s glutenin subunit 0154F22-S (Glu-B3) gene, complete cds. (Year: 2008).*
Meng et al., Genomic editing of intronic enhancers unveils their role in fine-tuning tissue-specific gene expression in *Arabidopsis thaliana*, 2021, The Plant Cell, vol. 33, pp. 1997-2014. (Year: 2021).*
Jores et al., Identification of Plant Enhancers and Their Constituent Elements by STARR-seq in Tobacco Leaves, 2020, The Plant Cell, vol. 32(7), pp. 2120-2131 (Year: 2020).*
Jores et al., Plant enhancers exhibit both cooperative and additive interactions among their functional elements, 2024, The Plant Cell, vol. 36(7), pp. 2570-2586 (Year: 2024).*
EBI Accession No. EM_EST:LU073199, Triticum aestivum mRNA, clone: CK053-K01, 5'-EST, cultivar Chinese Spring, Oct. 5, 2017.
Gotor et al., Analysis of three tissue-specific elements from the wheat Cab-1 enhancer, Plant J., 3(4):509-18 (Apr. 1993).
Huang, et al., "Intervening sequences increase efficiency of RNA 3' processing and accumulation of cytoplasmic RNA", Nucleic Acids Research, vol. 18, Issue 4, Feb. 25, 1990, pp. 937-947.
International Application No. PCT/EP2020/083879, International Search Report and Written Opinion, mailed Feb. 8, 2021.
Le Hir, et al., "How introns influence and enhance eukaryotic gene expression", Trends in biochemical sciences, vol. 28, Issue 4, Apr. 2003, pp. 215-220.
Marand et al., Towards genome-wide prediction and characterization of enhancers in plants, Biochim. Biophys. Acta Gene Regul. Mech., 1860(1):131-9 (Jan. 2017).
Nott, et al., "Splicing enhances translation in mammalian cells: an additional function of the exon junction complex", Genes & Development, vol. 18, Issue 2, 2004, pp. 210-222.
Ryan et al., The multiple origins of aluminium resistance in hexaploid wheat include Aegilops tauschii and more recent cis mutations to TaALMT1, Plant J., 63(3):446-55 (Nov. 2010).
Thomas et al., Identification of an enhancer element for the endosperm-specific expression of high molecular weight glutenin, Plant Cell, 2(12):1171-80 (Dec. 1990).

* cited by examiner

*Primary Examiner* — Bratislav Stankovic
*Assistant Examiner* — Christina L Meadows
(74) *Attorney, Agent, or Firm* — ArentFox Schiff LLP

(57) ABSTRACT

The present invention is in the field of plant molecular biology and provides methods for production of high expressing promoters and the production of plants with enhanced expression of nucleic acids wherein nucleic acid expression enhancing nucleic acids (NEENAs) are functionally linked to said promoters and/or introduced into plants.

Figure 1:
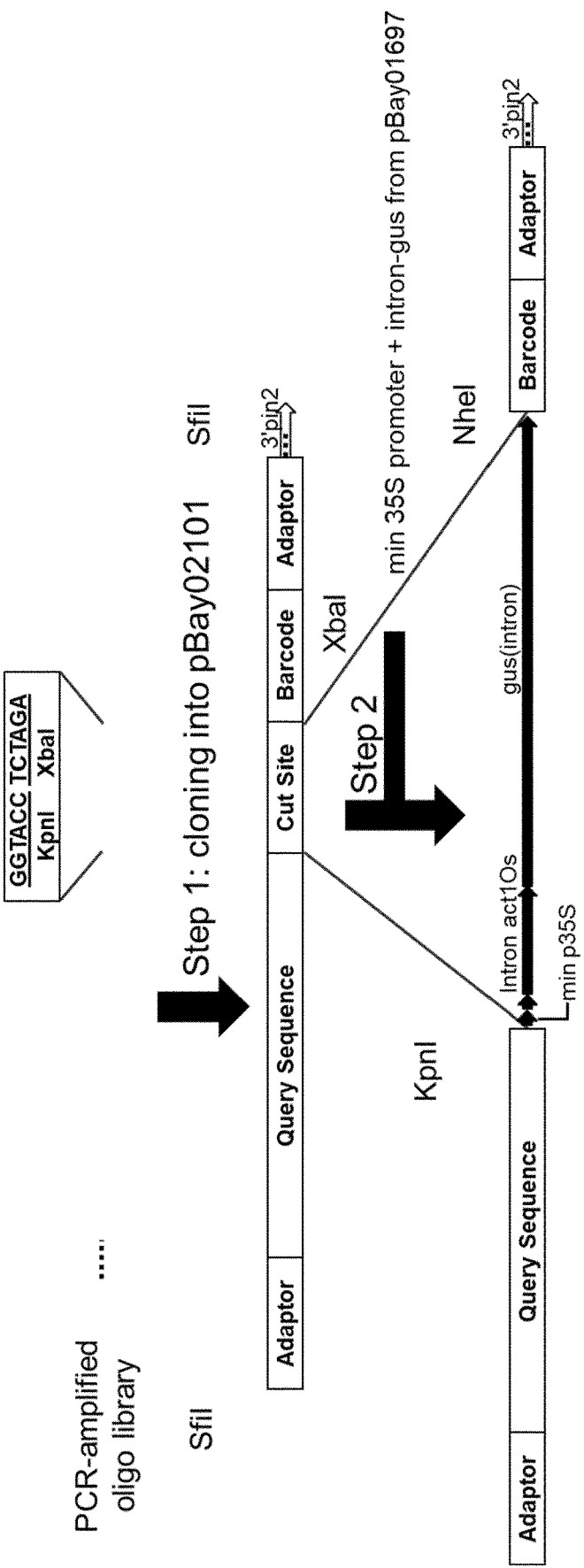

14 Claims, 5 Drawing Sheets
Specification includes a Sequence Listing.

REGULATORY NUCLEIC ACID MOLECULES FOR ENHANCING GENE EXPRESSION IN PLANTS

CROSS-REFERENCE TO RELATED APPLICATIONS

This is the U.S. national phase of International Application No. PCT/EP2020/083879, filed Nov. 30, 2020, which claims priority to European Patent Application No. 19213158.9, filed on Dec. 3, 2019.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "191374_SeqListing", which was created on May 16, 2022 and is 31,157 bytes in size. The subject matter of the Sequence Listing is incorporated herein in its entirety by reference.

DESCRIPTION OF THE INVENTION

The present invention is in the field of plant molecular biology and provides methods for production of high expressing promoters and the production of plants with enhanced expression of nucleic acids wherein nucleic acid expression enhancing nucleic acids (NEENAs) are functionally linked to said promoters and/or introduced into plants.

Expression of transgenes in plants is strongly affected by various external and internal factors resulting in a variable and unpredictable level of transgene expression. Often a high number of transformants must be produced and analyzed to identify lines with desirable expression strength. As transformation and screening of lines with desirable expression strength is costly and labor intensive there is a need for high expression of one or more transgenes in a plant. This problem is especially pronounced, when several genes must be coordinately expressed in a transgenic plant to achieve a specific effect as a plant has to be identified in which each gene is strongly expressed.

For example, expression of a transgene can vary significantly, depending on construct design and positional effects of the T-DNA insertion locus in individual transformation events. Strong promoters can partially overcome these challenges. However, availability of suitable promoters showing strong expression with the desired specificity is often limited. To ensure availability of sufficient promoters with desired expression specificity, the identification and characterization of additional promoters can help to close this gap. However, natural availability of promoters of the respective specificity and strength and the time-consuming characterization of promoter candidates impedes the identification of suitable new promoters.

To overcome these challenges, diverse genetic elements and/or motifs have been shown to positively affect gene expression. Among these, some introns have been recognized as genetic elements with a strong potential for improving gene expression. Although the mechanism is largely unknown, it has been shown that some introns positively affect the steady state amount of mature mRNA, possibly by enhanced transcriptional activity, improved mRNA maturation, enhanced nuclear mRNA export and/or improved translation initiation (e.g. Huang and Gorman, 1990, Nucleic Acid Research 18; Le Hir et al., 2003, Trend Biochem Sci 28; Nott et al., 2004, Genes Dev. 18).

Further, general enhancers have been identified that are not necessarily related to introns. Enhancers are important cis-regulatory DNA elements that regulate transcription programs by recruiting transcription factors and directing them to the promoters of target genes in a cell-type/tissue-specific manner. The expression of a gene can be regulated by one or multiple enhancers (Marand et al 2017; Biochimica and Biophysica Acta 1860(131-139). Enhancers are difficult to identify because of their unpredictable positions relative to their cognate promoters. They may be located upstream or downstream of the transcription start site of a certain expressed nucleic acid and may function at positions 5000 or more nucleotides away from the respective promoter. Remarkably, only a handful of enhancers have been identified in plant species largely due to the lack of general approaches for enhancer identification.

Furthermore, the development of genome editing techniques theoretically allows to also increase the expression level of endogenes by insertion of enhancers in promoters, untranslated regions or introns of endogenes. This approach is however impeded by the limited number of enhancers identified to date.

Nucleic acid molecules enhancing expression of functionally linked nucleic acids are in the present application described as "nucleic acid expression enhancing nucleic acids" (NEENA).

DETAILED DESCRIPTION OF THE INVENTION

A first embodiment of the invention comprises a method for the production of a promoter having enhanced expression strength comprising functionally linking to a promoter one or more nucleic acid expression enhancing nucleic acid (NEENA) molecule comprising i) the nucleic acid molecule having a sequence as defined in any one of SEQ ID NOs: 16 to 21, or ii) a nucleic acid molecule having a sequence with an identity of 80% or more to any one of the sequences as defined by SEQ ID NOs:16 to 21, preferably, the identity is 85% or more, more preferably the identity is 90% or more, even more preferably, the identity is 95% or more, 96% or more, 97% or more, 98% or more or 99% or more, in the most preferred embodiment, the identity is 100% to any one of the sequences as defined by SEQ ID NOs: 16 to 21, or iii) a nucleic acid molecule of 30 nucleotides or more, 40 nucleotides or more, 50 nucleotides or more or 100 nucleotides or more, hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably 65° C. to a nucleic acid molecule comprising at least 30, preferably at least 40, more preferably at least 50, even more preferably at least 100, most preferably at least 150 consecutive nucleotides of a transcription enhancing nucleotide sequence of any one SEQ ID NOs: 16 to 21, or the complement thereof. Preferably, said nucleic acid molecule is hybridizing under conditions equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C. to a nucleic acid molecule comprising at least 30, preferably at least 40, more preferably at least 50, even more preferably at least 100, most preferably at least 150 consecutive nucleotides of a transcription enhancing nucleotide sequence of any one of SEQ ID NOs: 16 to 21, or the complement thereof, more preferably, said nucleic acid molecule is hybridizing under conditions equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. to a nucleic acid molecule comprising at least 30, preferably at least 40, more preferably at least 50, even more preferably at least 100, most preferably at least 150 consecutive nucleotides of a transcription enhancing nucleotide sequence described by any one of the sequences of SEQ ID NOs: 16 to 21, or the complement thereof iv) a fragment of 30 or more consecutive bases, preferably 40 or more consecutive bases, more preferably 50 consecutive bases or more even more preferably 100 or more consecutive bases of a nucleic acid molecule of i) to iii) which has an expressing enhancing activity, for example 65% or more, preferably 70% or more, more preferably 75% or more, even more preferably 80% or more, 85% or more or 90% or more, in a most preferred embodiment it has 95% or more of the expression enhancing activity as the corresponding nucleic acid molecule having the sequence of any one of the sequences as defined by SEQ ID NOs: 16 to 21, or v) a nucleic acid molecule which is the complement or reverse complement of any of the previously mentioned nucleic acid molecules under i) to v).

In one embodiment, the one or more NEENA is heterologous to the promoter to which it is functionally linked.

In a further embodiment the NEENA of the invention is introduced into a promoter at a position which at the 5' end and/or 3' end is adjacent to sequences that are not naturally adjacent to the NEENA of the invention, e.g. in the genome of a WT plant.

In another embodiment of the invention 2 or less copies of the NEENA of the invention are introduced into the promoter.

In principal the NEENA may be functionally linked to any promoter such as tissue specific, inducible, developmental specific or constitutive promoters. The respective NEENA will lead to an enhanced expression of the heterologous nucleic acid under the control of the respective promoter to which the at least one NEENA is functionally linked to.

The one or more NEENA may be functionally linked to any promoter and will enhance expression of the nucleic acid molecule under control of said promoter. Constitutive promoters to be used in any method of the invention may be derived from plants, for example monocotyledonous or dicotyledonous plants, from bacteria and/or viruses or may be synthetic promoters. Constitutive promoters to be used are for example the Cassava vein mosaic virus-Promoter (Verdaguer B et al. (1996). PMB 31(6), 1129-39), the Subterrenean Clover Stunt Virus-Promoter (Boevink P, et al. (1995). Virology 207(2), 354-61), the *A. thaliana* histone 4A promoter in combination with the histone 3A intron (Chaboute et al. (1984). PMB 8(2), 179-91), the *B. napus* P450-dependent fatty acid omega-hydroxylase promoter (WO2016113333), the pAct10s promoter from rice (McElroy et al. (1990). Plant Cell 2(2), 163-71), the PcUbi-Promoter from *P. crispum* (WO 2003102198), the ZmUbi-Promoter from *Zea mays* (Christensen et al (1992). Plant Mol Biol. 18(4), 675-89), AtNit-promoter from the *A. thaliana* gene At3g44310 encoding nitrilase 1, the 34S-promoter from figwort mosaic virus (Sanger et al., 1990, PMB 14(3)), the 35S-promoter from Cauliflower mosaic virus (Odell et al (1985). Nature 313(6005), 810-2), the nos (Depicker et al (1982). J Mol Appl Genet. 1(6), 561-73) and ocs-promoter derived from *Agrobacterium tumefaciens*, the ScBV-promoter (U.S. Pat. No. 5,994,123), the SUPER-promoter (Lee et al. 2007, Plant. Phys. 145), the AtFNR-promoter from the *A. thaliana* gene At5g66190 encoding the ferredoxin NADH reductase, the ptxA promoter from *Pisum sativum* (WO2005085450), the AtTPT-promoter from the *A. thaliana* gene At5g46110 encoding the triose phosphate translocator, the bidirectional AtOASTL-promoter from the *A. thaliana* genes At4g14880 and At4g14890, the PRO0194 promoter from the *A. thaliana* gene At1g13440 encoding the glyceraldehyde-3-phosphate dehydrogenase, the PRO0162 promoter from the *A. thaliana* gene At3g52930 encoding the fructose-bis-phosphate aldolase, the AHAS-promoter (WO2008124495), the CaffeoylCoA-MT promoter and the OsCP12 from rice (WO2006084868) or the pGOS2 promoter from rice (de Pater et al. (1992). Plant J. 2(6), 837-44).

Tissue or developmental specific or inducible promoters to be used in any method of the invention may be derived from plants, for example monocotyledonous or dicotyledonous plants, from bacteria and/or viruses or may be synthetic promoters. Tissue or developmental specific or inducible promoters to be used are for example the seed specific and/or seed-preferential promoters for example the High Molecular Weight Glutenin Bx17 promoter from *T. aestivum* (Reddy P and Appels R (1993) Theor Appl Genet. 85(5), 616-24), High Molecular Weight Glutenin 1 Dx5 promoter from *T. aestivum* (Lamacchia et al. (2001) J Exp Bot. 52(355), 243-50), the plastidic AGPase promoter from *T. aestivum* (Thorneycroft et al. (2003) Plant Biotechnol J. 1(4), 259-70), the hordein B1 promoter from *Hordeum vulgare* (Brandt et al. (1985) Carlsberg Research Communications 50, 333), the SBP-promoter from *Vicia faba* (WO2000026388), the Unknown Seed Protein-promoter (USP) from *Vicia faba* (WO2003092362), the napin promoter from *Brassica napus* (EP0255378), the conlinin-promoter from *Linum usitatissmum* (WO2001016340), the promoter from the *A. thaliana* gene At5g01670 encoding the peroxiredoxin like protein (WO2006089950), the promoter of the peroxiredoxin like protein from *Linum usitatissmum* (WO2006089950), the globulin like protein promoter from *Brassica napus* (Roh et al., 2014, Journal of the Korean Society for Applied Biological Chemistry 57(5)), the arcelin5-1 promoter from *Phaseolus vulgaris* (WO 2012077020), the Zein promoter from *Zea mays* (Shepherd and Scott Biotechnol Appl Biochem. 2009, 52(3)), the globulin promoter from *Zea mays* (Mei et al., 2004, Maydica 49(4)), the pKG86 promoter from *Zea mays* (WO 2010122110), the leaf specific ST-LS1 promoter from *Solanum tuberosum* (Stockhaus et al (1989) EMBO J. 8(9), 2445-51), the leaf specific thioredoxin promoter from *Oryza sativa* (Fukuda et al. (2005) Plant Cell Physiol. 46(11), 1779-86), the root specific or root preferential promoters Pbtg-26D from *G. hirsutum* (WO2017/025282), PGL4 and 5 from *Zea mays* (EP1862473) or Pzrp2 from *Zea mays* (Held et al. (1997) PMG 35(3), 367-375), the inducible promoters Phpr1 from *A. thaliana* (Wang et al. (2009) Molecular Plant 2(1), 191-200), the rd29a promoter from *A. thaliana* (Yamaguchi-Shinozaki K and Shinozaki K (1994) Plant Cell 6(2), 251-64), the proteinase inhibitor promoter from *Zea mays* (Cordero et al (1994) Plant J. 6(2), 141-50), or the fiber specific or preferential promoters from *G. hirsutum* as described in WO2012093032, US2013081154, WO2004065571, WO2008083969 or WO2012136788.

The high expression promoters of the invention functionally linked to a NEENA may be employed in any plant comprising for example moss, fern, gymnosperm or angiosperm, for example monocotyledonous or dicotyledonous plant. In a preferred embodiment said promoter of the invention functionally linked to a NEENA may be employed in monocotyledonous or dicotyledonous plants, preferably crop plant such as corn, soy, canola, cotton, potato, sugar beet, rice, wheat, sorghum, barley, musa, sugarcane, *miscanthus* and the like. In a preferred embodiment of the invention, said promoter which is functionally linked to a NEENA may be employed in monocotyledonous crop plants such as corn, rice, wheat, sorghum, musa, *miscanthus*, sugarcane or barley. In an especially preferred embodiment the promoter functionally linked to a NEENA may be employed in wheat.

A high expressing promoter as used in the application means for example a promoter which is functionally linked to a NEENA causing enhanced expression of the promoter in a plant or part thereof wherein the accumulation of RNA or rate of synthesis of RNA derived from the nucleic acid molecule under the control of the respective promoter functionally linked to a NEENA is higher, preferably significantly higher than the expression caused by the same promoter lacking a NEENA of the invention. Preferably the amount of RNA of the respective nucleic acid and/or the rate of RNA synthesis and/or the RNA stability in a plant is increased 50% or more, for example 100% or more, preferably 200% or more, more preferably 5 fold or more, even more preferably 10 fold or more, most preferably 20 fold or more for example 50 fold compared to a control plant of same age grown under the same conditions comprising the same promoter the latter not being functionally linked to a NEENA of the invention.

When used herein, significantly higher refers to statistical significance the skilled person is aware how to determine, for example by applying statistical tests such as the t-test to the respective data sets.

Methods for detecting expression conferred by a promoter are known in the art. For example, the promoter may be functionally linked to a marker gene such as GUS, GFP or luciferase and the activity of the respective protein encoded by the respective marker gene may be determined in the plant or part thereof. As a representative example, the method for detecting luciferase is described in detail below. Other methods are for example measuring the steady state level or synthesis rate of RNA of the nucleic acid molecule controlled by the promoter by methods known in the art, for example Northern blot analysis, qPCR, run-on assays or other methods described in the art.

A skilled person is aware of various methods for functionally linking two or more nucleic acid molecules. Such methods may encompass restriction/ligation, ligase independent cloning, recombineering, recombination or synthesis. Other methods may be employed to functionally link two or more nucleic acid molecules.

A further embodiment of the present invention is a method for producing a plant or part thereof with, compared to a respective control plant or part thereof, enhanced expression of one or more nucleic acid molecule comprising the steps of introducing into the plant or part thereof one or more NEENA comprising a nucleic acid molecule as defined above under i) to v) and functionally linking said one or more NEENA to a promoter and to a nucleic acid molecule being under the control of said promoter, wherein the NEENA is heterologous to said nucleic acid molecule.

The NEENA may be heterologous to the nucleic acid molecule which is under the control of said promoter to which the NEENA is functionally linked or it may be heterologous to both the promoter and the nucleic acid molecule under the control of said promoter.

The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. For example, a NEENA of the invention is in its natural environment functionally linked to its native promoter, whereas in the present invention it is linked to another promoter which might be derived from the same organism, a different organism or might be a synthetic promoter such as the SUPER-promoter. It may also mean that the NEENA of the present invention is linked to its native promoter but the nucleic acid molecule under control of said promoter is heterologous to the promoter comprising its native NEENA. It is in addition to be understood that the promoter and/or the nucleic acid molecule under the control of said promoter functionally linked to a NEENA of the invention are heterologous to said NEENA as their sequence has been manipulated by for example mutation such as insertions, deletions and the forth so that the natural sequence of the promoter and/or the nucleic acid molecule under control of said promoter is modified and therefore have become heterologous to a NEENA of the invention. It may also be understood that the NEENA is heterologous to the nucleic acid to which it is functionally linked when the NEENA is functionally linked to its native promoter wherein the position of the NEENA in relation to said promoter is changed so that the promoter shows higher expression after such manipulation.

A plant exhibiting enhanced expression of a nucleic acid molecule as meant herein means a plant having a higher, preferably statistically significant higher expression of a nucleic acid molecule compared to a control plant grown under the same conditions without the respective NEENA functionally linked to the respective nucleic acid molecule. Such control plant may be a wild-type plant or a transgenic plant comprising the same promoter controlling the same gene as in the plant of the invention wherein the promoter is not linked to a NEENA of the invention.

Producing a plant as used herein comprises methods for stable transformation such as introducing a recombinant DNA construct into a plant or part thereof by means of *Agrobacterium* mediated transformation, protoplast transformation, particle bombardment or the like and optionally subsequent regeneration of a transgenic plant.

It also comprises methods for transient transformation of a plant or part thereof such as viral infection or *Agrobacterium* infiltration. A skilled person is aware of further methods for stable and/or transient transformation of a plant or part thereof.

Approaches such as breeding methods, protoplast fusion or recombination techniques using a donor DNA might also be employed for production of a plant of the invention and are covered herewith. For example, a single strand break (nick) or a double strand break may be introduced into the genome of a plant using recombinant technologies known in the art such as TALEN (WO12138939, WO12138927); Zinc finger proteins (WO02057293, WO05084190), homing endonucleases (WO11104382, WO14199358) or nucleic acid guided nucleases such as AGO, Cas9 or Cas12 (WO13141680, WO13176772, WO14093595, WO15157534 or WO16205711). Together with the introduction of such single- or double strand break inducing agents, one or more donor DNA (WO13176772, WO14089290) may be introduced into the plant or part thereof comprising the NEENA molecule flanked by nucleic acid molecules comprising sequences essentially identical or essentially complementary to the regions adjacent to the nick or double strand break thereby facilitating homologous recombination and introducing the NEENA molecule into the genome of the plant or part thereof.

Further, the sequence of a NEENA of the invention may be introduced into the genome and functionally linked to the respective heterologous promoter by introducing into the genome a series of point mutations using technologies such as deaminases (WO0058480, WO18027078) and the like which may be directed to a specific region in the genome of a plant or part thereof by fusing the mutating polypeptide portion e.g. a deaminase or glycosidase to a DNA binding polypeptide such as, for example a TALEN, a Zinc finger protein, a homing endonuclease or an RNA guided nuclease, nickase or inactivated nuclease such as Cas9 or Cas12, as described in WO15089406, US2017321210, WO15133554 or WO17070632. By application of these methods, the NEENA sequence is introduced into the genome without introduction of a heterologous molecule but the NEENA sequence replaces another sequence in the genome. Such technologies are encompassed by the term "integrate" or "introducing" an NEENA sequence or "integrating" or "introducing" a NEENA molecule into the genome and functionally linking such sequences and/or molecules to a heterologous promoter.

The method of the invention may be applied to any plant, for example gymnosperm or angiosperm, preferably angiosperm, for example dicotyledonous or monocotyledonous plants, preferably monocotyledonous plants. Preferred monocotyledonous plants are for example corn, wheat, rice, barley, sorghum, musa, sugarcane, *miscanthus* and *brachypodium*, especially preferred monocotyledonous plants are corn, wheat and rice, most preferred is wheat. Preferred dicotyledonous plants are for example soy, rape seed, canola, linseed, cotton, potato, sugar beet, *tagetes* and *Arabidopsis*, especially preferred dicotyledonous plants are soy, rape seed, canola and potato.

In one embodiment of the method of the invention the one or more NEENA molecule or NEENA sequence is integrated into the genome of a plant or part thereof by applying genome editing technologies.

In a further embodiment of the method of the invention the genome editing technology comprises the introduction of single or double strand breaks at the position the NEENA molecule is to be integrated into the genome using nucleic acid guided nucleases, for example AGO, Cas9 or Cas12 nucleases, TALEN, homing endonucleases or Zinc finger proteins and further the introduction of a DNA repair template comprising the NEENA molecule and at its 3' and 5' end sequences essentially identical or essentially complementary to the sequences upstream and/or downstream of the single or double strand break facilitating recombination at the position of the single or double strand break. Preferably, the essentially identical or essentially complementary sequences are each individually at least 1000, at least 500 bases, at least 450 bases, at least 400 bases, at least 350 bases, at least 300 bases, at least 250 bases, at least 200 bases, at least 150 bases, at least 100 bases or at least 50 bases long. Preferably, the identity or complementarity of the sequences is at least 50%, at least 60%, at least 70% at least 75%, at least 80%, at least 85%, at least 90%, at least 95%, at least 96%, at least 97%, at least 98%, at least 98 or at least 99% identical or complementary to the respective genomic region with which they recombine.

In a further embodiment of the method of the invention the genome editing technology comprises introduction of point mutations in the genome of the plant or part thereof thereby introducing the sequence of the NEENA in the plant genome. This can for example be achieved by introducing DNA binding proteins, for example Zinc finger proteins, TALE proteins or a nucleic acid guided nuclease, for example Cas9, Cas12 (Cpfl) or AGO functionally bound to a cytidine deaminase (WO17070633) or adenine deaminase (WO18027078).

In one embodiment of the invention, the methods as defined above are comprising the steps of
 a) introducing one or more NEENA comprising a nucleic acid molecule as defined above in i) to v) into a plant or part thereof and
 b) integrating said one or more NEENA into the genome of said plant or part thereof whereby said one or more NEENA is functionally linked to an endogenous expressed nucleic acid heterologous to said one or more NEENA and optionally
 c) regenerating a plant or part thereof comprising said one or more NEENA from said transformed cell.

The NEENA may be heterologous to the nucleic acid molecule which is under the control of said promoter to which the NEENA is functionally linked or it may be heterologous to both the promoter and the nucleic acid molecule under the control of said promoter.

The one or more NEENA molecule may be introduced into the plant or part thereof by means of particle bombardment, protoplast electroporation, virus infection, *Agrobacterium* mediated transformation, CRISPR/Cas or any other approach known in the art. The NEENA molecule may be introduced integrated for example into a plasmid or viral DNA or viral RNA or a donor DNA in a CRISPR/Cas approach. The NEENA molecule may also be comprised on a BAC, YAC or artificial chromosome prior to introduction into the plant or part of the plant. It may be also introduced as a linear nucleic acid molecule comprising the NEENA sequence wherein additional sequences may be present adjacent to the NEENA sequence on the nucleic acid molecule. These sequences neighboring the NEENA sequence may be from about 20 bp, for example 20 bp to several hundred base pairs, for example 100 bp or more and may facilitate integration into the genome for example by homologous recombination. Any other method for genome integration may be employed, be it targeted integration approaches, such as homologous recombination or random integration approaches, such as illegitimate recombination.

The endogenous expressed nucleic acid to which the NEENA molecule may be functionally linked may be any nucleic acid, preferably any expressed nucleic acid molecule. The nucleic acid molecule may be a protein coding nucleic acid molecule or a non-coding molecule such as antisense RNA, rRNA, tRNA, miRNA, ta-siRNA, siRNA, dsRNA, snRNA, snoRNA or any other noncoding RNA known in the art.

A further way to perform the methods of the invention may be to
 a) provide an expression construct comprising one or more NEENA comprising a nucleic acid molecule as defined above in i) to v) functionally linked to a promoter as defined above and to one or more nucleic acid molecule the latter being heterologous to said one or more NEENA and which is under the control of said promoter and b) integrate said expression construct comprising said one or more NEENA into the genome of said plant or part thereof and optionally c) regenerate a plant or part thereof comprising said one or more expression construct from said transformed plant or part thereof.

The NEENA may be heterologous to the nucleic acid molecule which is under the control of said promoter to which the NEENA is functionally linked or it may be heterologous to both the promoter and the nucleic acid molecule under the control of said promoter.

The expression construct may be integrated into the genome of the respective plant with any method known in the art. The integration may be random using methods such as particle bombardment or *Agrobacterium* mediated transformation or CRISPR/Cas applications. In a preferred embodiment, the integration is via targeted integration for example by homologous recombination. The latter method would allow integrating the expression construct comprising a high expression promoter functionally linked to a NEENA into a favorable genome region. Favorable genome regions are for example genome regions known to comprise genes that are highly expressed for example in seeds and hence may increase expression derived from said expression construct compared to a genome region which shows no transcriptional activity.

In another preferred embodiment said one or more NEENA is functionally linked to a promoter close to the transcription start site of said heterologous nucleic acid molecule.

Close to the transcription start site as meant herein comprises functionally linking one or more NEENA to a promoter 5000 bp or less, 4000 bp or less, 3000 or less, 2500 bp or less, preferentially 2000 bp or less, more preferred 1500 bp or less, even more preferred 1000 bp or less and most preferred 500 bp or less away from the transcription start site of said heterologous nucleic acid molecule. It is to be understood that the NEENA may be integrated upstream or downstream in the respective distance from the transcription start site of the respective promoter. Hence, the one or more NEENA may be included in the primary transcript of the respective heterologous nucleic acid under control of the preferably constitutive promoter the one or more NEENA is functionally linked to or it may be integrated in the promoter molecule. If the NEENA is integrated downstream of the transcription start site of the respective promoter, the integration site is preferably in the 5' UTR, the 3' UTR or intron of the heterologous nucleic acid under the control of the promoter, most preferentially it is integrated in the 1$^{st}$ intron of the respective heterologous nucleic acid.

Preferentially the one or more NEENA is integrated in the promoter, the 5' UTR or the 1st intron or the NEENA is replacing a part in the promoter, the 5' UTR or 1$^{st}$ intron.

In another aspect of the invention wherein said one or more NEENA is linked to the 7A trehalose-6-phosphate phosphatase (T6PP) gene (WO/2018/113702, SEQ ID NO. 22), the NEENA may be inserted at about 200 bp, at about 397 bp, at about 676 bp, or at about 1000 bp upstream of the translation start codon. Said one or more NEENA may be inserted into the 7A trehalose-6-phosphate phosphatase (T6PP) gene at a position between 150 and 250 bp, between 350 and 450 bp, between 620 and 720 bp or between 950 and 1000 bp upstream of the translation start codon.

A further embodiment of the invention comprises a recombinant expression construct comprising one or more NEENA comprising a nucleic acid molecule as defined above in i) to v).

The recombinant expression construct may further comprise one or more promoter to which the one or more NEENA is functionally linked and optionally one or more expressed nucleic acid molecule the latter being heterologous to said one or more NEENA.

The NEENA may be heterologous to the nucleic acid molecule which is under the control of said promoter to which the NEENA is functionally linked or it may be heterologous to both the promoter and the nucleic acid molecule under the control of said promoter.

The expression construct may comprise one or more, for example two or more, for example 5 or more, such as 10 or more combinations of promoters functionally linked to a NEENA and a nucleic acid molecule to be expressed heterologous to the respective NEENA. The expression construct may also comprise further promoters not comprising a NEENA functionally linked to nucleic acid molecules to be expressed homologous or heterologous to the respective promoter.

A recombinant expression vector comprising one or more recombinant expression construct as defined above is another embodiment of the invention. A multitude of expression vectors that may be used in the present invention are known to a skilled person. Methods for introducing such a vector comprising such an expression construct comprising for example a promoter functionally linked to a NEENA and optionally other elements such as a terminator into the genome of a plant and for recovering transgenic plants from a transformed cell are also well known in the art. Depending on the method used for the transformation of a plant or part thereof the entire vector might be integrated into the genome of said plant or part thereof or certain components of the vector might be integrated into the genome, such as, for example a T-DNA.

A transgenic plant or part thereof comprising one or more heterologous NEENA as defined above in i) to v) is also enclosed in this invention. A NEENA is to be understood as being heterologous to the plant if it is synthetic, derived from another organism or the same organism but its natural genomic localization is rendered compared to a control plant, for example a wild type plant. It is to be understood, that a rendered genomic localization means the NEENA is located on another chromosome or on the same chromosome but 10 kb or more, for example 10 kb, preferably 5 kb or more, for example 5 kb, more preferably 1000 bp or more, for example 1000 bp, even more preferably 500 bp or more, for example 500 bp, especially preferably 100 bp or more, for example 100 bp, most preferably 10 bp or more, for example 10 bp dislocated from its natural genomic localization in a wild type plant.

A transgenic cell or transgenic plant or part thereof comprising a recombinant expression vector as defined above or a recombinant expression construct as defined above is a further embodiment of the invention. The transgenic cell, transgenic plant or part thereof may be selected from the group consisting of bacteria, fungi, yeasts or plant, insect or mammalian cells or plants. Preferably the transgenic cells are bacteria, fungi, yeasts or plant cells. Preferred bacteria are Enterobacteria such as *E. coli* and bacteria of the genus Agrobacteria, for example *Agrobacterium tumefaciens* and *Agrobacterium rhizogenes*. Preferred plants are monocotyledonous or dicotyledonous plants for example monocotyledonous or dicotyledonous crop plants such as corn, soy, canola, cotton, potato, sugar beet, rice, wheat, sorghum, barley, *miscanthus*, musa, sugarcane and the like. Preferred crop plants are corn, rice, wheat, soy, canola, cotton or potato. Especially preferred dicotyledonous crop plants are soy, canola, cotton or potato.

Especially preferred monocotyledonous crop plants are corn, wheat and rice. Most preferred is wheat.

A transgenic cell culture, transgenic seed, parts or propagation material derived from a transgenic cell or plant or part thereof as defined above comprising said heterologous NEENA as defined above in i) to v) or said recombinant expression construct or said recombinant vector as defined above are other embodiments of the invention.

Transgenic parts or propagation material as meant herein comprise all tissues and organs, for example leaf, stem and fruit as well as material that is useful for propagation and/or regeneration of plants such as cuttings, scions, layers, branches or shoots comprising the respective NEENA, recombinant expression construct or recombinant vector.

A further embodiment of the invention is the use of the NEENA as defined above in i) to v) or the recombinant construct or recombinant vector as defined above for enhancing expression in plants or parts thereof.

The application at hand provides gene expression enhancing nucleic acid molecules, constructs comprising one or more promoter functionally linked to one or more NEENA. Additionally, use of such gene expression enhancing nucleic acid molecules and expression constructs, expression vectors, transgenic plants or parts thereof and transgenic cells comprising such gene expression enhancing nucleic acid molecules are provided.

A use of a transgenic cell culture, transgenic seed, parts or propagation material derived from a transgenic cell or plant or part thereof as defined above for the production of foodstuffs, animal feeds, seeds, pharmaceuticals or fine chemicals is also enclosed in this invention.

Definitions

Abbreviations: NEENA—nucleic acid expression enhancing nucleic acid, GFP—green fluorescence protein, GUS—beta-Glucuronidase, BAP—6-benzylaminopurine; 2,4-D—2,4-dichlorophenoxyacetic acid; MS—Murashige and Skoog medium; NAA—1-naphtaleneacetic acid; MES, 2-(N-morpholino-ethanesulfonic acid, IAA indole acetic acid; Kan: Kanamycin sulfate; GA3—Gibberellic acid; Timentin™: ticarcillin disodium/clavulanate potassium, microl: Microliter.

It is to be understood that this invention is not limited to the particular methodology or protocols. It is also to be understood that the terminology used herein is for the purpose of describing particular embodiments only and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Antiparallel: "Antiparallel" refers herein to two nucleotide sequences paired through hydrogen bonds between complementary base residues with phosphodiester bonds running in the 5'-3' direction in one nucleotide sequence and in the 3'-5' direction in the other nucleotide sequence.

Antisense: The term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene mRNA molecule or single stranded genomic DNA through Watson-Crick base pairing) or that is complementary to a target DNA molecule such as, for example genomic DNA present in the host cell.

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Double-stranded RNA: A "double-stranded RNA" molecule or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule.

Endogenous: An "endogenous" nucleotide sequence refers to a nucleotide sequence, which is present in the genome of the untransformed plant cell.

Enhanced expression: "enhance" or "increase" the expression of a nucleic acid molecule in a plant cell are used equivalently herein and mean that the level of expression of the nucleic acid molecule in a plant, part of a plant or plant cell after applying a method of the present invention is higher than its expression in the plant, part of the plant or plant cell before applying the method, or compared to a reference plant lacking a recombinant nucleic acid molecule of the invention. For example, the reference plant is comprising the same construct which is only lacking the respective NEENA. The term "enhanced" or "increased" as used herein are synonymous and means herein higher, preferably significantly higher expression of the nucleic acid molecule to be expressed. As used herein, an "enhancement" or "increase" of the level of an agent such as a protein, mRNA or RNA means that the level is increased relative to a substantially identical plant, part of a plant or plant cell grown under substantially identical conditions, lacking a recombinant nucleic acid molecule of the invention, for example lacking the NEENA molecule, the recombinant construct or recombinant vector of the invention. As used herein, "enhancement" or "increase" of the level of an agent, such as for example a preRNA, mRNA, rRNA, tRNA, snoRNA, snRNA expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a cell or organism lacking a recombinant nucleic acid molecule of the invention. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a plant or plant cell. Depending on the type of the induced protein product, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254). As one example for quantifying the activity of a protein, the detection of luciferase activity is described in the Examples below.

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Expression construct: "Expression construct" as used herein mean a DNA sequence capable of directing expression of a particular nucleotide sequence in an appropriate part of a plant or plant cell, comprising a promoter functional in said part of a plant or plant cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example RNAa, siRNA, snoRNA, snRNA, microRNA, ta-siRNA or any other noncoding regulatory RNA, in the sense or antisense direction. The expression construct comprising the nucleotide sequence of interest may be chimeric, meaning that one or more of its components is heterologous with respect to one or more of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a constitutive promoter or of an inducible promoter, which initiates transcription only when the host cell is exposed to some particular external stimulus. In the case of a plant, the promoter can also be specific to a particular tissue or organ or stage of development.

Foreign: The term "foreign" refers to any nucleic acid molecule (e.g., gene sequence) which is introduced into the genome of a cell by experimental manipulations and may include sequences found in that cell so long as the introduced sequence contains some modification (e.g., a point mutation, the presence of a selectable marker gene, etc.) and is therefore distinct relative to the naturally-occurring sequence.

Functional linkage: The term "functional linkage" or "functionally linked" is to be understood as meaning, for example, the sequential arrangement of a regulatory element (e.g. a promoter) with a nucleic acid sequence to be expressed and, if appropriate, further regulatory elements (such as e.g., a terminator or a NEENA) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

Gene: The term "gene" refers to a region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Heterologous: The term "heterologous" with respect to a nucleic acid molecule or DNA refers to a nucleic acid molecule which is operably linked to, or is manipulated to become operably linked to, a second nucleic acid molecule, e.g. a promoter to which it is not operably linked in nature, e.g. in the genome of a WT plant, or to which it is operably linked at a different location or position in nature, e.g. in the genome of a WT plant.

Preferably the term "heterologous" with respect to a nucleic acid molecule or DNA, e.g. a NEENA refers to a nucleic acid molecule which is operably linked to, or is manipulated to become operably linked to, a second nucleic acid molecule, e.g. a promoter to which it is not operably linked in nature.

A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene— becomes a transgenic expression construct when it is modified by non-natural, synthetic "artificial" methods such as, for example, mutagenization. Such methods have been described (U.S. Pat. No. 5,565,350; WO 00/15815). For example, a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

High expression promoter: A "high expression promoter" as used herein means a promoter causing expression in a plant or part thereof wherein the accumulation or rate of synthesis of RNA or stability of RNA derived from the nucleic acid molecule under the control of the respective promoter is higher, preferably significantly higher than the expression caused by the promoter lacking the NEENA of the invention. Preferably the amount of RNA and/or the rate of RNA synthesis and/or stability of RNA is increased 50% or more, for example 100% or more, preferably 200% or more, more preferably 5-fold or more, even more preferably 10-fold or more, most preferably 20-fold or more for example 50-fold relative to a promoter lacking a NEENA of the invention.

Hybridization: The term "hybridization" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point (Tm) for the specific sequence at a defined ionic strength and pH. Medium stringency conditions are when the temperature is 20° C. below Tm, and high stringency conditions are when the temperature is 10° C. below Tm. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore, medium stringency hybridisation conditions may sometimes be needed to identify such nucleic acid molecules.

The "Tm" is the temperature under defined ionic strength and pH, at which 50% of the target sequence hybridises to a perfectly matched probe. The Tm is dependent upon the solution conditions and the base composition and length of the probe. For example, longer sequences hybridise specifically at higher temperatures. The maximum rate of hybridisation is obtained from about 16° C. up to 32° C. below Tm. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

DNA-DNA hybrids (Meinkoth and Wahl, Anal. Biochem., 138: 267-284, 1984):
$Tm=81.5° C.+16.6×\log[Na+]a+0.41×\%[G/Cb]-500×[Lc]-1-0.61×\%$ formamide DNA-RNA or RNA-RNA hybrids:
$Tm=79.8+18.5 (\log 10[Na+]a)+0.58 (\% G/Cb)+11.8 (\% G/Cb)2-820/Lc$ oligo-DNA or oligo-RNAd hybrids:
For <20 nucleotides: $Tm=2 (In)$
For 20-35 nucleotides: $Tm=22+1.46 (In)$
a or for other monovalent cation, but only accurate in the 0.01-0.4 M range.
b only accurate for % GC in the 30% to 75% range.
c L=length of duplex in base pairs.
d Oligo, oligonucleotide; In, effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For nonrelated probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 μg/ml denatured, fragmented salmon sperm DNA, 0.5% sodium pyrophosphate. Another example of high stringency conditions is hybridisation at 65° C. in 0.1×SSC comprising 0.1 SDS and optionally 5×Denhardt's reagent, 100 μg/ml denatured, fragmented salmon sperm DNA, 0.5% sodium pyrophosphate, followed by the washing at 65° C. in 0.3×SSC.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

"Identity": "Identity" when used in respect to the comparison of two or more nucleic acid or amino acid molecules means that the sequences of said molecules share a certain degree of sequence similarity, the sequences being partially identical.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

The following example is meant to illustrate two nucleotide sequences, but the same calculations apply to protein sequences:

Seq A: AAGATACTG length: 9 bases
Seq B: GATCTGA length: 7 bases
Hence, the shorter sequence is sequence B.
Producing a pairwise global alignment which is showing both sequences over their complete lengths results in

```
Seq A: AAGATACTG-
            ||| |||
Seq B: --GAT-CTGA
```

The "|" symbol in the alignment indicates identical residues (which means bases for DNA or amino acids for proteins). The number of identical residues is 6.

The "-" symbol in the alignment indicates gaps. The number of gaps introduced by alignment within the Seq B is 1. The number of gaps introduced by alignment at borders of Seq B is 2, and at borders of Seq A is 1.

The alignment length showing the aligned sequences over their complete length is 10.

Producing a pairwise alignment which is showing the shorter sequence over its complete length according to the invention consequently results in:

```
Seq A: GATACTG-
       ||| |||
Seq B: GAT-CTGA
```

Producing a pairwise alignment which is showing sequence A over its complete length according to the invention consequently results in:

```
Seq A: AAGATACTG
          ||| |||
Seq B: --GAT-CTG
```

Producing a pairwise alignment which is showing sequence B over its complete length according to the invention consequently results in:

```
Seq A: GATACTG-
       ||| |||
Seq B: GAT-CTGA
```

The alignment length showing the shorter sequence over its complete length is 8 (one gap is present which is factored in the alignment length of the shorter sequence).

Accordingly, the alignment length showing Seq A over its complete length would be 9 (meaning Seq A is the sequence of the invention).

Accordingly, the alignment length showing Seq B over its complete length would be 8 (meaning Seq B is the sequence of the invention).

After aligning two sequences, in a second step, an identity value is determined from the alignment produced. For purposes of this description, percent identity is calculated by %-identity=(identical residues/length of the alignment region which is showing the respective sequence of this invention over its complete length)*100. Thus, sequence identity in relation to comparison of two amino acid sequences according to this embodiment is calculated by dividing the number of identical residues by the length of the alignment region which is showing the respective sequence of this invention over its complete length. This value is multiplied with 100 to give "%-identity". According to the example provided above, %-identity is: for Seq A being the sequence of the invention (6/9)*100=66.7%; for Seq B being the sequence of the invention (6/8)*100=75%.

Intron: refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5' or 3' untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG. Furthermore, in plants, two examples of AU-AC introns have been described: the fourteenth intron of the RecA-like protein gene and the seventh intron of the G5 gene from *Arabidopsis thaliana* are AT-AC introns. Pre-mRNAs containing introns have three short sequences that are—beside other sequences—essential for the intron to be accurately spliced. These sequences are the 5' splice-site, the 3' splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron is comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branch point. The branchpoint sequence is important in splicing and splice-site selection in plants. The branchpoint sequence is usually located 10-60 nucleotides upstream of the 3' splice site.

Isogenic: organisms (e.g., plants), which are genetically identical, except that they may differ by the presence or absence of a heterologous DNA sequence.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring polynucleotide or polypeptide present in a living plant is not isolated, but the same polynucleotide or polypeptide, separated from some or all of the coexisting materials in the natural system, is isolated. Such polynucleotides can be part of a vector and/or such polynucleotides or polypeptides could be part of a composition and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 16 includes, by way of example, such nucleic acid sequences in cells which ordinarily contain SEQ ID NO:16 where the nucleic acid sequence is in a chromosomal or extrachromosomal location different from that of natural cells or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Minimal Promoter: promoter elements, particularly a TATA element, that are inactive or that have greatly reduced promoter activity in the absence of upstream activation. In the presence of a suitable transcription factor, the minimal promoter functions to permit transcription.

NEENA: see "Nucleic acid expression enhancing nucleic acid".

Non-coding: The term "non-coding" refers to sequences of nucleic acid molecules that do not encode part or all of an expressed protein. Non-coding sequences include but are not limited to introns, enhancers, promoter regions, 3' untranslated regions, and 5' untranslated regions.

Nucleic acid expression enhancing nucleic acid (NEENA): The term "nucleic acid expression enhancing nucleic acid" refers to a sequence and/or a nucleic acid molecule of a specific sequence having the intrinsic property to enhance expression of a nucleic acid under the control of a promoter to which the NEENA is functionally linked. Unlike promoter sequences, the NEENA as such is not able to drive expression. In order to fulfill the function of enhancing expression of a nucleic acid molecule functionally linked to the NEENA, the NEENA itself has to be functionally linked to a promoter. In distinction to enhancer sequences known in the art, the NEENA is acting in cis but not in trans and has to be located close to the transcription start site of the nucleic acid to be expressed.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Plant: is generally understood as meaning any eukaryotic single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophyceae, Rhodophyceae, Myxophyceae, Xanthophyceae, Bacillariophyceae (diatoms), and Euglenophyceae. Preferred are plants which are used for food or feed purpose such as the families of the Leguminosae such as pea, alfalfa and soya; Gramineae such as rice, maize, wheat, barley, sorghum, millet, rye, triticale, or oats; the family of the Umbelliferae, especially the genus *Daucus*, very especially the species *carota* (carrot) and *Apium*, very especially the species *Graveolens* dulce (celery) and many others; the family of the Solanaceae, especially the genus Lycopersicon, very especially the species *esculentum* (tomato) and the genus *Solanum*, very especially the species *tuberosum* (potato) and *melongena* (egg plant), and many others (such as tobacco); and the genus *Capsicum*, very especially the species *annuum* (peppers) and many others; the family of the Leguminosae, especially the genus *Glycine*, very especially the species *max* (soybean), alfalfa, pea, lucerne, beans or peanut and many others; and the family of the Cruciferae (Brassicacae), especially the genus *Brassica*, very especially the species *napus* (oil seed rape), *campestris* (beet), *oleracea* cv Tastie (cabbage), *oleracea* cv Snowball Y (cauliflower) and *oleracea* cv Emperor (broccoli); and of the genus *Arabidopsis*, very especially the species thaliana and many others; the family of the Compositae, especially the genus *Lactuca*, very especially the species *sativa* (lettuce) and many others; the family of the Asteraceae such as sunflower, *Tagetes*, lettuce or *Calendula* and many other; the family of the Cucurbitaceae such as melon, pumpkin/squash or zucchini, and linseed. Further preferred are cotton, sugar cane, hemp, flax, chillies, and the various tree, nut and wine species.

Polypeptide: The terms "polypeptide", "peptide", "oligopeptide", "polypeptide", "gene product", "expression product" and "protein" are used interchangeably herein to refer to a polymer or oligomer of consecutive amino acid residues.

Pre-protein: Protein, which is normally targeted to a cellular organelle, such as a chloroplast, and still comprising its transit peptide.

Primary transcript: The term "primary transcript" as used herein refers to a premature RNA transcript of a gene. A "primary transcript" for example still comprises introns and/or is not yet comprising a polyA tail or a cap structure and/or is missing other modifications necessary for its correct function as transcript such as for example trimming or editing.

Promoter. The terms "promoter", or "promoter sequence" are equivalents and as used herein, refer to a DNA sequence which when ligated to a nucleotide sequence of interest is capable of controlling the transcription of the nucleotide sequence of interest into RNA. Such promoters can for example be found in the following public databases world wide web at grassius.org/grasspromdb. html, world wide web at mendel.cs.rhul.ac.uk/mendel.php?topic=plantprom, world wide web at ppdb.gene.nagoya-u.ac.jp/cgi-bin/index.cgi. Promoters listed there may be addressed with the methods of the invention and are herewith included by reference. A promoter is located 5' (i.e., upstream), proximal to the transcriptional start site of a nucleotide sequence of interest whose transcription into mRNA it controls and provides a site for specific binding by RNA polymerase and other transcription factors for initiation of transcription. Said promoter comprises for example the at least 10 kb, for example 5 kb or 2 kb proximal to the transcription start site. It may also comprise the at least 1500 bp proximal to the transcriptional start site, preferably the at least 1000 bp, more preferably the at least 500 bp, even more preferably the at least 400 bp, the at least 300 bp, the at least 200 bp or the at least 100 bp. In a further preferred embodiment, the promoter comprises the at least 50 bp proximal to the transcription start site, for example, at least 25 bp. The promoter does not comprise exon and/or intron regions or 5' untranslated regions. The promoter may for example be heterologous or homologous to the respective plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). A plant specific promoter is a promoter suitable for regulating expression in a plant. It may be derived from a plant but also from plant pathogens or it might be a synthetic promoter designed by man. If a promoter is an inducible promoter, then the rate of transcription increases in response to an inducing agent. Also, the promoter may be regulated in a tissue-specific or tissue preferred manner such that it is only or predominantly active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue The term "cell type specific" when applied to a promoter also means a promoter capable of promoting selective expression of a nucleotide sequence of interest in a region within a single tissue Cell type specificity of a promoter may be assessed using methods well known in the art, e.g., GUS activity staining, GFP protein or immunohistochemical staining. The term "constitutive" when made in reference to a promoter or the expression derived from a promoter means that the promoter is capable of directing transcription of an operably linked nucleic acid molecule in the absence of a stimulus (e.g., heat shock, chemicals, light, etc.) in the majority of plant tissues and cells throughout substantially the entire lifespan of a plant or part of a plant. Typically, constitutive promoters are capable of directing expression of a transgene in substantially any cell and any tissue.

Promoter specificity: The term "specificity" when referring to a promoter means the pattern of expression conferred by the respective promoter. The specificity describes the tissues and/or developmental status of a plant or part thereof, in which the promoter is conferring expression of the nucleic acid molecule under the control of the respective promoter. Specificity of a promoter may also comprise the environmental conditions, under which the promoter may be activated or down-regulated such as induction or repression by biological or environmental stresses such as cold, drought, wounding or infection.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. Recombinant nucleic acid molecules may also comprise molecules, which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

Sense: The term "sense" is understood to mean a nucleic acid molecule having a sequence which is complementary or identical to a target sequence, for example a sequence which binds to a protein transcription factor and which is involved in the expression of a given gene. According to a preferred embodiment, the nucleic acid molecule comprises a gene of interest and elements allowing the expression of the said gene of interest.

Significant increase or decrease: An increase or decrease, for example in enzymatic activity or in gene expression, that is larger than the margin of error inherent in the measurement technique, preferably an increase or decrease by about 2-fold or greater of the activity of the control enzyme or expression in the control cell, more preferably an increase or decrease by about 5-fold or greater, and most preferably an increase or decrease by about 10-fold or greater.

Small nucleic acid molecules: "small nucleic acid molecules" are understood as molecules consisting of nucleic acids or derivatives thereof such as RNA or DNA. They may be double-stranded or single-stranded and are between about 15 and about 30 bp, for example between 15 and 30 bp, more preferred between about 19 and about 26 bp, for example between 19 and 26 bp, even more preferred between about 20 and about 25 bp for example between 20 and 25 bp. In a especially preferred embodiment the oligonucleotides are between about 21 and about 24 bp, for example between 21 and 24 bp. In a most preferred embodiment, the small nucleic acid molecules are about 21 bp and about 24 bp, for example 21 bp and 24 bp.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the latter being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the chromosomal DNA of the host cell. Another type of vector is an episomal vector, i.e., a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences recognized by any RNA polymerase, including mitochondrial RNA polymerase, RNA pol I, RNA pol II, and RNA pol III. These vectors can be used to transcribe the desired RNA molecule in the cell according to this invention. A plant transformation vector is to be understood as a vector suitable in the process of plant transformation.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

FIGURES

FIG. 1: Cloning strategy of the MPRA expression library.

Figure 2:
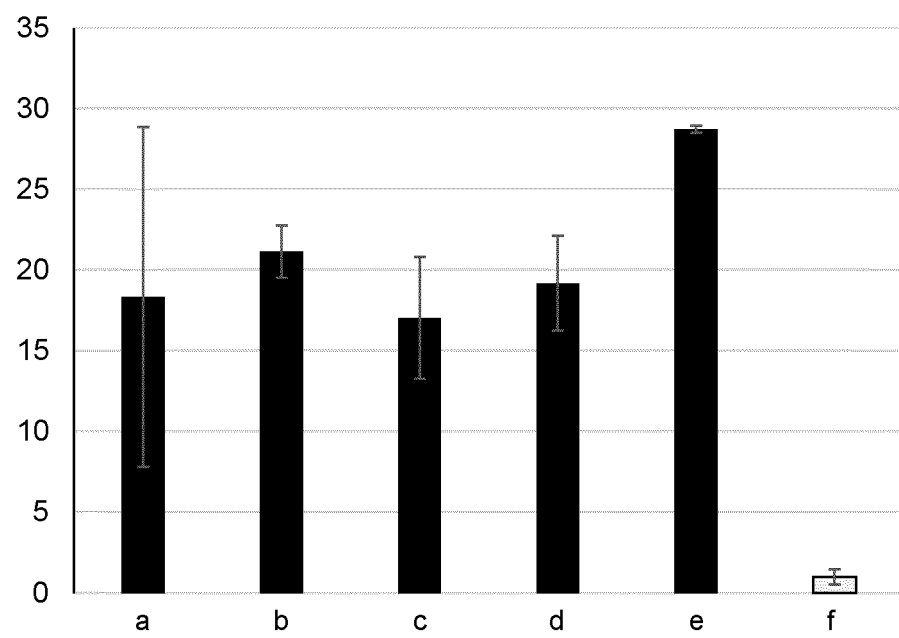

FIG. 2: Impact of candidate enhancers on activity of the minimal CaMV 35S promoter in transiently transformed wheat protoplasts. The vertical axis shows the relative promoter activity. The horizontal axis legend shows the number of the enhancer fragment as follows: a: EN5128, b: EN3638, c: EN2516, d: EN2161/2, e: EN3233, f: none. GUS activities were corrected for variation in protoplast transfection efficiency using the luciferase activities of a co-introduced pKA63 plasmid. Activity of the promoter without enhancer (none) was set at 1.

Figure 3:
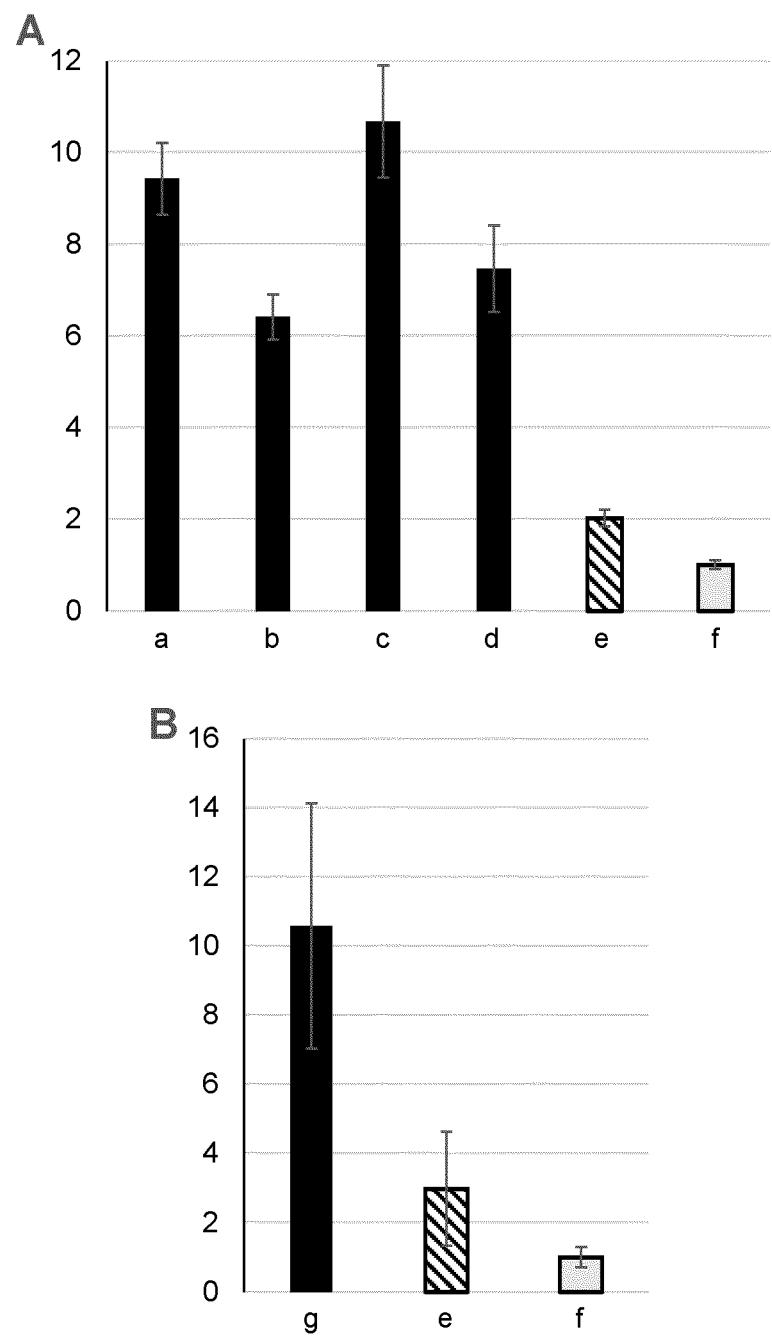

FIG. 3: Impact of candidate enhancers on activity of the wheat T6PP promoter in transiently transformed wheat protoplasts. The vertical axis shows the relative promoter activity. The horizontal axis legend shows the number of the enhancer fragment as follows: a: EN5128, b: EN3638, c: EN2516, d: EN2161/2, e: ALMT1, f: none, g: EN3233. GUS activities were corrected for variation in protoplast transfection efficiency using the luciferase activities of a co-introduced pKA63 plasmid. Activity of the promoter without enhancer (none) was set at 1.

Figure 4:
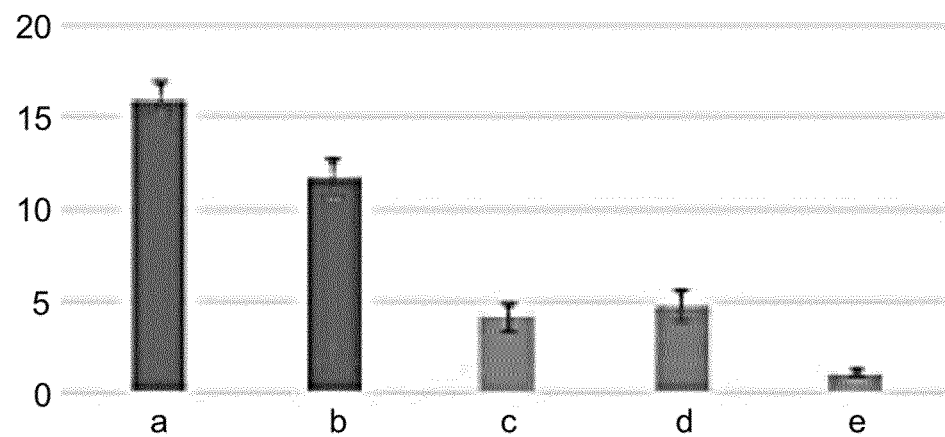

FIG. 4: Impact of the orientation of the wheat enhancers on activity of the wheat T6PP promoter in transiently transformed wheat protoplasts. The vertical axis shows the relative promoter activity. The horizontal axis shows the number of the selected enhancer and the orientation as follows: a: EN3233, b: EN3233 reverse orientation, c: EN5128 reverse orientation, d: EN2516 reverse orientation, e: no enhancer. Activity of the promoter without enhancer (none) was set at 1.

Figure 5:
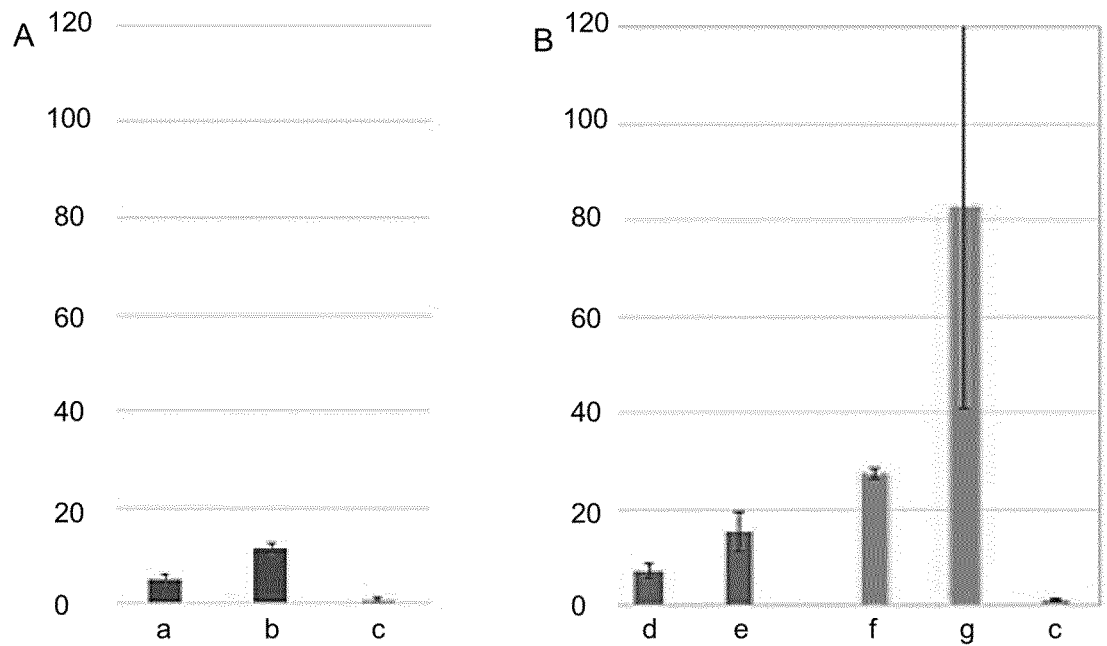

FIG. 5: Impact of the duplication of the wheat enhancers on activity of the wheat T6PP promoter in transiently transformed wheat protoplasts. The vertical axis shows the relative promoter activity. The horizontal axis shows the number of the selected enhancer and whether it is duplicated as follows: a: EN2516, b: EN2516 duplicated, c: no enhancer, d: EN5128, e: EN5128 duplicated, f: EN3233, g: EN3233 duplicated. Activity of the promoter without enhancer (none) was set at 1.

EXAMPLES

Chemicals and Common Methods

Unless indicated otherwise, cloning procedures carried out for the purposes of the present invention including restriction digest, agarose gel electrophoresis, purification of nucleic acids, Ligation of nucleic acids, transformation, selection and cultivation of bacterial cells were performed as described (Sambrook et al., 1989). Sequence analyses of recombinant DNA were performed with a laser fluorescence DNA sequencer (Applied Biosystems®, Foster City, Calif., USA) using the Sanger technology (Sanger et al., 1977). Unless described otherwise, chemicals and reagents were obtained from Sigma Aldrich® (Sigma Aldrich, St. Louis, USA), from Promega® (Madison, Wis., USA), Duchefa (Haarlem, The Netherlands) or Invitrogen® (Carlsbad, Calif., USA). Restriction endonucleases were from New England Biolabs® (Ipswich, Mass., USA) or Roche Diagnostics® GmbH (Penzberg, Germany). Oligonucleotides were synthesized by Eurofins® MWG Operon (Ebersberg, Germany).

Example 1: Discovery of New Candidate Enhancer Sequences from the Wheat Genome

To identify novel wheat enhancer sequences, 500 genes that either are highly expressed (average CPM above 500) or have a medium expression level (average CPM between 100 and 500) with a low gene expression variability between wheat tissues (low Coefficient of variation), were selected from the wheat genome (IWGSC version 1.0 2017). Gene expression levels were normalized using the TMM method (edgeR).

From these 500 genes, sequences of the putative promoter, the first intron and the 3'UTR, if available in the genome sequence, were extracted based on the genome annotation and an improved annotation pipeline. For the introns the 5' 10 nt and the 3' 20 nt were excluded. Only those sequences that were at least 144 nt long were retained. In total, 1392 sequence features were retained.

These 1392 sequences were digested in silico at the NheI, XbaI, KpnI, PvuI and SfiI sites. The resulting promoter and intron sequences were split into 144-nt long fragments with a 20-nt overlap, except for the 2 most 3' fragments for which the overlap is such that the 3'end of the last 144-nt fragment coincides with the 3'end of the original sequence. The 3' UTR sequences were split in the same way in overlapping 139-nt long fragments and CTAGC was added to the 5'end of each 3'UTR fragment, resulting again in 144-nt long sequence fragments. This whole process resulted in 9919 sequences that are 144 nt in length. 10 sequences (SEQ ID NO 1 to 10) were added to the list. These are sequences from which the impact on expression in wheat protoplasts was known from previous experiments. The P35S and the ALMT1 3' sequences increase expression of a 35S minimal promoter >10- and 6-fold, respectively, whereas the lambda insulator and ALMT1 5' sequences do not increase expression of this minimal promoter. The resulting 9929 sequences were cloned into an MPRA library (Melnikov et al. 2014, J. Vis. Exp. (90), e51719) to screen for sequences with promoter enhancing activity. Each sequence was linked to 5 different unique 11-nt long bar codes. The bar codes do not contain AATAAT, AATAAA, ATTTA, TTTTT, restriction sites for NheI, XbaI, KpnI, PvuI and SfiI, differ by at least 2 nt, have no base repeats longer than 2 nt, and do not start with TC. 200-nt long oligos were synthesized containing each of the 49645 query sequence—bar code combinations and the sequences required for amplification and cloning of the library into the expression vectors (FIG. 1). In a first cloning step, the amplified oligo library was cloned upstream of the 3' pin2 of pBay02101 (SEQ ID No 11) using the SfiI restriction recognition sites. Next, a Kpn-NheI fragment containing the minimal 35S promoter, the *petunia* cab22L leader sequence, the rice actin-1 intron and the gus coding sequence from pBay01697 (SEQ ID No 12), was cloned in the KpnI and XbaI sites between the query sequence and the bar code. The resulting plasmid library contained the query sequences upstream of the minimal 35S promoter and the linked bar codes in the 3'UTR of the GUS gene. Sequencing of 48 clones from the plasmid library showed that 44 of the clones contained the expected query sequences whereas 4 clones contained shorter-than-expected inserts.

The resulting plasmid library was transfected into wheat mesophyll protoplasts (4 transfections of 80 g of plasmid DNA in one million protoplasts). Transfected protoplasts were incubated for 6 hrs and collected for RNA isolation. Total RNA was isolated using a Sigma® plant RNA isolation kit. The isolated RNA was eluted in a total volume of 130 µl and had a concentration of 0.54 g/l. A DNase treatment was performed on this RNA using the Turbo DNase kit from Ambion® applying 2 µl of DNase for 30 min at 37° C.

Following an RNA denaturation step (5 min at 65° C.), cDNA was synthesized with the Superscript® III First Strand Synthesis kit from Thermofisher® using oligo dT and 40 µl (=18 µg) of total RNA in a final volume of 100 µl. cDNA synthesis was performed for 50 min at 50° C. followed by 5 min at 80° C. Following cDNA synthesis, RNA was removed using RNase H for 20 min at 37° C.

In a next step, the bar code containing regions of the cDNA (15 µl RT reaction) and of the plasmid library DNA (1 ng) were amplified by PCR using primers MPRA_SfiI (SEQ ID No 13) and MPRA_R3 (SEQ ID No 14) and InFusion DNA polymerase in HF buffer (final volume of 60 µl).

PCR Conditions:
95° C. 2 min
25 cycli of 98° C. 30 seconds, 55° C. 30 seconds, 72° C. 30 seconds
72° C. 2 min The PCR reactions were cleaned up using a 0.8× Agencourt AMPure bead cleanup and eluted in 30 µl water. Appropriate amounts of PCR product were loaded on the MiSeq for 26-bp single read sequencing. For each sample, more than 30 Mio reads were obtained. From these data, the frequency of each bar code within the RNA of the transfected protoplasts as well as within the transfected plasmid DNA library was deduced. The ratio of the bar code abundance in the RNA versus the abundance in the plasmid library DNA is a measure for the expression enhancing activity of the test sequence that is linked to the specific bar code. As each test sequence is linked to 5 different bar codes, each test sequence has 5 RNA/DNA ratios. The median value was used as a measure for the enhancer activity of the tested sequence. A paired t-test was used to test the significance ($p<0.05$) of the expression increase of specific sequences.

TABLE 1

Comparison of known enhancer effect of control sequences with observed RNA/DNA ratios in the MPRA expression library.

| Control sequence | Known enhancer activity | Observed RNA/DNA ratio |
| --- | --- | --- |
| P35S −208 to −65 | >10-fold | 20.05 |
| ALMT1 3' | 6-fold | 5.31 |
| ALMT1 5' | none | 0.39 |
| Lambda insulator | none | 0.106 |

Results from the control sequences (see Table 1) showed that the 35S enhancer and the ALMT1 3' sequence had high RNA/DNA ratios, around 20 and 5 respectively, whereas the nonfunctional ALMT1 5' and Lambda insulator sequences had RNA/DNA ratios that are well below 1. This showed that the RNA/DNA ratios are consistent with the known enhancer activity of these control sequences.

Table 2 shows 6 query sequences that had an RNA/DNA ratio that is above that of the wheat ALMT1 3' enhancer and do not contain sequences that are present in high copy number in the wheat genome. These sequences include 2 highly overlapping fragments (EN2161 and EN2162) from the promoter of a low molecular weight glutenin subunit gene, that are shifted by only 20 nt and thus overlap by 124 nt.

Example 2: Validation of Enhancer Sequences in Wheat Protoplasts

The first 4 sequences listed in Table 2, plus the combined EN2161+EN2162 sequence (164 nt fragment) were cloned upstream of the minimal 35S promoter and the gus coding sequence in plasmid pBay01697 for validation in wheat protoplasts. The resulting plasmids were introduced in wheat mesophyll protoplasts and protein was extracted and GUS activities determined following an overnight incubation of the protoplasts. To correct for differences in introduction efficiency, GUS activities of transfected wheat protoplasts were divided by the luciferase activities from a co-introduced control vector having the firefly luciferase gene under control of the maize ubiquitin promoter (pKA63, SEQ ID NO 15). Wheat protoplast preparation and PEG transfection of wheat protoplasts was performed according to Shang et al. (2014, Nature protocols 9(10), 2395-2410).

The resulting data show that all the candidate enhancers effectively increased expression from a minimal 35S promoter (FIG. 2).

Example 3: Impact of the Wheat Enhancers on Wheat Promoter Activity

The same set of enhancers were tested with a 1-kb promoter fragment of the 7A trehalose-6-phosphate phosphatase (T6PP) gene (WO/2018/113702, SEQ ID NO. 22). The enhancer fragments were inserted 200 nt upstream of the translation start codon, which is the location in the promoter at which the highest expression increase was obtained when inserting the ALMT1B enhancer (EP 19173869.9). Transient expression of the resulting plasmids in wheat protoplasts showed that all the enhancer fragments increase expression from the wheat T6PP promoter between 6- and 10-fold, which is clearly higher than the ALMT1B enhancer (FIG. 3).

Example 4: Impact of the Orientation of the Wheat Enhancers on Wheat Promoter Activity Three of the enhancers (EN3233, SEQ ID NO: 19, EN2516, SEQ ID NO: 18, and EN5128, SEQ ID NO: 16) were inserted in the opposite orientation in the promoter of the wheat T6PP gene. Both enhancers remained functional, i.e. increased expression from the wheat promoter (FIG. 4).

Example 5: Impact of Duplication of the Wheat Enhancers on Wheat Promoter Activity Three of the enhancers (EN3233, SEQ ID NO: 19, EN5128, SEQ ID NO: 16 and EN2516, SEQ ID NO: 18) have been each inserted in a duplicated manner, ie inserting twice said enhancer at one location, in the promoter of the wheat T6PP gene. For both enhancers, duplication increased their activity significantly compared to when only one enhancer is inserted in the same promoter (FIG. 5).

Example 6: MPRA Experiment to Map Functional Elements within the Enhancer Sequences An MPRA library was synthesized that contains the selected enhancer sequences (EN3233 and EN5128) and each single-nt mutant thereof, together with 2 positive (35S enhancer and ALMT1 3') and 2 negative (ALMT1 5' and lambda insulator fragment) control sequences. Each sequence is linked to 19 different barcodes. These sequences were cloned in a plasmid library with the enhancer sequences upstream of the minimal 35S promoter and the bar codes downstream of a gus gene that is under the control of the minimal 35S promoter with linked enhancer. The plasmid library was transfected into wheat protoplasts and the frequency of the bar codes in the expressed RNA was compared to that in the plasmid library as a measure for the activity of the linked enhancer sequence. Based on these results, sequence motifs were selected from EN3233 and EN5128.

Motifs and mutations therein affecting EN3233 enhancer activity: Two motifs have been identified as comprising the most important positions for enhancer activity:
  First motif: CAGGTTCAACGAACGC (SEQ ID NO: 23), nucleotides corresponding to the nucleotides at position 79 to 94 of SEQ ID NO: 19
  Second motif: GTCCACCAGCGCCAGCCGCCT (SEQ ID NO: 24), nucleotides corresponding to the nucleotides at position 106 to 126 of SEQ ID NO: 19.

Therefore a fragment of SEQ ID NO: 19 is functional when it comprises the first motif of nucleotides corresponding to the nucleotides at position 79 to 94 of SEQ ID NO: 19, the second motif of nucleotides corresponding to the nucleotides at position 106 to 126 of SEQ ID NO: 19 or both motifs.

Some mutations had a negative effect on the enhancer activity. In the first motif the enhancer activity was reduced compared to the one of SEQ ID NO: 19 by replacing the nucleotide at position 79, 88 or 92 with an A or G nucleotide, replacing the nucleotide at position 80, 85, 87 or 91 with a T or G nucleotide, replacing the nucleotide at position 81, 83 or 84 with a C or A nucleotide, replacing the nucleotide at position 82 with a T or C nucleotide, replacing the nucleotide at position 86 or 90 with a G or C nucleotide, replacing the nucleotide at position 89 with a T or A nucleotide, replacing the nucleotide at position 93 with a T nucleotide, or replacing the nucleotide at position 94 with a G nucleotide. In the second motif the enhancer activity was reduced compared to the one of SEQ ID NO: 19 by replacing the nucleotide at position 106, 113 or 114 with a T or C nucleotide, replacing the nucleotide at position 107, 110 or 119 with a C or G nucleotide, replacing the nucleotide at position 108 with a G nucleotide, replacing the nucleotide at position 109, 115 or 116 with a T or A nucleotide, replacing the nucleotide at position 111, 121 or 125 with an A or G nucleotide, replacing the nucleotide at position 112, 117, 118, 122 or 124 with a G or T nucleotide, replacing the nucleotide at position 120 with any other nucleotide (A, T or C), replacing the nucleotide at position 123 with a T nucleotide, or replacing the nucleotide at position 126 with a C nucleotide.

Some mutations however demonstrated a positive effect on the enhancer activity. In the first motif the enhancer activity was increased compared to the one of SEQ ID NO: 19 by replacing the nucleotide at position 94 with a T nucleotide. In the second motif the enhancer activity was increased compared to the one of SEQ ID NO: 19 by replacing the nucleotide at position 106 with an A nucleotide, replacing the nucleotide at position 109 with a G nucleotide, or replacing the nucleotide at position 114 with an A nucleotide.

Motifs and mutations therein affecting EN5128 enhancer activity:
  One weak motif has been identified as comprising the most important positions for enhancer activity: ATTGG, nucleotides corresponding to the nucleotides at position 135 to 139 of SEQ ID NO: 16.

Therefore a fragment of SEQ ID NO: 16 is functional when it comprises this motif of nucleotides corresponding to the nucleotides at position 135 to 139 of SEQ ID NO: 16.

Some mutations had a negative effect on the enhancer activity. The enhancer activity was reduced compared to the one of SEQ ID NO: 16 by replacing the nucleotide at position 138 with a T nucleotide.

Some mutations had a positive effect on the enhancer activity. The enhancer activity was increased compared to the one of SEQ ID NO: 16 by replacing the nucleotide at position 138 with a C nucleotide.

TABLE 2

List of MPRA query sequences that were validated for enhancer activity by transfection in wheat protoplasts. If elements originate from the same gene this is marked with a grey background. Sequence names include 3 fields, separated by _:
field 1, prom: promoter
field 2, IWGSC genome annotation
field 3, the chromosome and coordinates of the sequence.

| Gene ID | Gene annotation | Type | ratio | P value | Number | Seq ID | Sequence coordinates |
|---|---|---|---|---|---|---|---|
| CS6A01G101800 | calnexin homolog | promoter | 8.80 | 0.01574 | EN5128 | 16 | prom__TraesCS6A01G101800__chr6A:70569513-70569656 |
| CS1B01G131300 | dihydrolipoyl dehydrogenase 1, mitochondrial-like | promoter | 8.41 | 0.02180 | EN3638 | 17 | prom__TraesCS1B01G131300__chr1B:163100404-163100547 |
| CS2B01G386900 | remorin-like | promoter | 8.17 | 0.00603 | EN2516 | 18 | prom__TraesCS2B01G386900__chr2B:550039229-550039372 |
| CS5D01G027600 | cysteine synthase | promoter | 12.05 | 0.05373 | EN3233 | 19 | prom__TraesCS5D01G027600__chr5D:25277779-25277922 |
| CS1B01G011700 | low molecular weight glutenin subunit | promoter | 5.33 | 0.02681 | EN2161 | 20 | prom__TraesCS1B01G011700__chr1B:5688160-5688303 |
| CS1B01G011700 | low molecular weight glutenin subunit | promoter | 9.95 | 0.10660 | EN2162 | 21 | prom__TraesCS1B01G011700__chr1B:5688180-5688323 |

What is claimed is:

1. A method for enhancing expression derived from a plant promoter comprising functionally linking to a promoter one or more nucleic acid expression enhancing nucleic acid (NEENA) molecule heterologous to said promoter comprising
   the nucleic acid molecule having the sequence of SEQ ID NO: 19, wherein
   the nucleotide at position 94 is a C or a T nucleotide,
   the nucleotide at position 106 is a G or an A nucleotide,
   the nucleotide at position 109 is a C or a G nucleotide, or
   the nucleotide at position 114 is a G or an A nucleotide.

2. A method for producing a plant or part thereof with, compared to a respective control plant or part thereof, enhanced expression of one or more nucleic acid molecule comprising the steps of
   a) introducing into the plant or part thereof one or more NEENA molecule comprising a nucleic acid molecule as defined in claim 1;
   and
   b) functionally linking said one or more NEENA molecule to a promoter and to a nucleic acid molecule being under the control of said promoter, wherein the NEENA molecule is heterologous to said promoter.

3. The method of claim 1, comprising the steps of
   a) introducing the one or more NEENA molecule comprising a nucleic acid molecule as defined in claim 1 into a plant or part thereof and
   b) integrating said one or more NEENA molecule into the genome of said plant or part thereof whereby said one or more NEENA molecule is functionally linked to an endogenous promoter heterologous to said one or more NEENA molecule.

4. The method of claim 1, comprising the steps of
   a) providing an expression construct comprising one or more NEENA molecule comprising a nucleic acid molecule as defined in claim 1 functionally linked to a promoter heterologous to said one or more NEENA molecule and
   b) integrating said expression construct comprising said one or more NEENA molecule into the genome of said plant or part thereof.

5. The method of claim 1, wherein said one or more NEENA molecule is functionally linked to a promoter upstream of the translational start site of the nucleic acid molecule the expression of which is under the control of said promoter.

6. The method of claim 1, wherein said one or more NEENA molecule is functionally linked to a promoter within the 5'UTR of the nucleic acid molecule the expression of which is under the control of said promoter.

7. The method of claim 1, wherein said one or more NEENA molecule is functionally linked to a tissue specific, developmental specific or inducible promoter within the 5'UTR of the nucleic acid molecule the expression of which is under the control of said promoter.

8. A recombinant expression construct comprising a nucleic acid expression enhancing nucleic acid (NEENA) molecule,
   the nucleic acid molecule having the sequence of SEQ ID NO: 19, wherein
   the nucleotide at position 94 is a C or a T nucleotide,
   the nucleotide at position 106 is a G or an A nucleotide,
   the nucleotide at position 109 is a C or a G nucleotide, or
   the nucleotide at position 114 is a G or an A nucleotide,
   functionally linked to one or more promoter and one or more expressed nucleic acid molecule wherein the promoter is heterologous to said one or more NEENA molecule.

9. A recombinant expression vector comprising one or more recombinant expression construct of claim 8.

10. A transgenic cell or transgenic plant or transgenic plant part comprising the recombinant expression construct of claim 8.

11. The transgenic cell, transgenic plant or transgenic plant part of claim 10, selected or derived from the group consisting of bacteria, and plants.

12. A transgenic cell culture, transgenic seed, parts or propagation material derived from the transgenic cell or transgenic plant or transgenic plant part of claim 11 comprising the recombinant expression construct.

13. The method of claim 3, further comprising c) regenerating a plant or part thereof comprising said one or more NEENA molecule.

14. The method of claim 4, further comprising c) regenerating a plant or part thereof comprising said one or more expression construct.

* * * * *

SEQUENCE LISTING

<160> NUMBER OF SEQ ID NOS: 24

<210> SEQ ID NO 1
<211> LENGTH: 144
<212> TYPE: DNA
<213> ORGANISM: Cauliflower mosaic virus

<400> SEQUENCE: 1
ctatcgttca agatgccct gccgacagtg gtcccaaaga tggaccccca cccacgagga    60
gcatcgtgga aaaagaagac gttccaacca cgtcttcaaa gcaagtggat tgatgtgata   120
tctccactga cgtaagggat gacg                                         144

<210> SEQ ID NO 2
<211> LENGTH: 144
<212> TYPE: DNA
<213> ORGANISM: Escherichia virus Lambda

<400> SEQUENCE: 2
cagggtgtgg aagtaggaca ttttcatgtc aggccacttc tttccggagc ggggttttgc    60
tatcacgttg tgaacttctg aagcggtgat gacgccgagc cgtaatttgt gccacgcatc   120
atccccctgt tcgacagctc tcac                                         144

<210> SEQ ID NO 3
<211> LENGTH: 144
<212> TYPE: DNA
<213> ORGANISM: Triticum aestivum

<400> SEQUENCE: 3
cacgccggct cgtacgtagc gccgtcgtgg tgtcccctgg cgactgattt gggcagcgcg    60
gtggatgggt taggaggaat gtgagcgcgc catgtgtttg tccgccagtg cctaactgcc   120
gcactgcctc aaaaggcgcg tgct                                         144

<210> SEQ ID NO 4
<211> LENGTH: 144
<212> TYPE: DNA
<213> ORGANISM: Triticum aestivum

<400> SEQUENCE: 4
gcgcgtgcta gggtactgta cttaattagc agcgccggca ggggcgaggt cgtatctggc    60
agcggcgtgc cctgaggagg tcggatccgg cggaggcgcg cgctcggaga ggccgtatcc   120
agcggaggcg accggcaggg gggg                                         144

<210> SEQ ID NO 5
<211> LENGTH: 144
<212> TYPE: DNA
<213> ORGANISM: Oryza sativa

<400> SEQUENCE: 5
tcggtctcga tctttggcct tggtagtttg ggtgggcgag aggcggcttc gtgcgcgccc    60
agatcggtgc gcgggagggg cgggatctcg cggctggggc tctcgccggc gtggatccgg   120
cccggatctc gcgggaatg gggc                                          144

<210> SEQ ID NO 6
<211> LENGTH: 144
<212> TYPE: DNA
<213> ORGANISM: Oryza sativa

<400> SEQUENCE: 6

```
gccggcgtgg atccggcccg gatctcgcgg ggaatggggc tctcggatgt agatctgcga    60
tccgccgttg ttgggggaga tgatgggggg tttaaaattt ccgccatgct aaacaagatc   120
aggaagaggg gaaaagggca ctat                                          144
```

<210> SEQ ID NO 7
<211> LENGTH: 144
<212> TYPE: DNA
<213> ORGANISM: Oryza sativa

<400> SEQUENCE: 7

```
catgctaaac aagatcagga agaggggaaa agggcactat ggtttatatt tttatatatt    60
tctgctgctt cgtcaggctt agatgtgcta gatctttctt tcttcttttt gtgggtagaa   120
tttgaatccc tcagcattgt tcat                                          144
```

<210> SEQ ID NO 8
<211> LENGTH: 144
<212> TYPE: DNA
<213> ORGANISM: Oryza sativa

<400> SEQUENCE: 8

```
ctggagatga gattttaggg ggtttattag gtgaggtggc tgtgtttgtg aaatcctagg    60
aattatctct caagtcaatc taacgatgag atataactga ggttctggtt ttaatcacaa   120
actcatataa ccaatttatt gaaa                                          144
```

<210> SEQ ID NO 9
<211> LENGTH: 144
<212> TYPE: DNA
<213> ORGANISM: Oryza sativa

<400> SEQUENCE: 9

```
ctagcgggct caagccctaa actgaacggg atagtcatgc tcaaaccagt ttctacacgg    60
caagaattta ctgattctta acttttgca gtcaattaaa ttatggtttt tatatatgta   120
attttgtatc cgattgtagg gatc                                          144
```

<210> SEQ ID NO 10
<211> LENGTH: 144
<212> TYPE: DNA
<213> ORGANISM: Glycine max

<400> SEQUENCE: 10

```
ctagcaggag actgacatag attggaggag acattttgta taataggatc taggagactg    60
acatagattg gaggagacat tttgtataat aggatctagg agactgacat agattggagg   120
agacattttg tataataggg gatc                                          144
```

<210> SEQ ID NO 11
<211> LENGTH: 6180
<212> TYPE: DNA
<213> ORGANISM: Artificial Sequence
<220> FEATURE:
<223> OTHER INFORMATION: vector

<400> SEQUENCE: 11

```
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg   120 ttggcgggtg tcgggctgg cttaactatg cggcatcaga gcagattgta ctgagagtgc   180
```

```
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt gggcctaact ggccgcgatc      420
gctacgtacc tgcaggcccg ggttaattaa gcggccgcaa catggagtca aaaattcaga      480
tcgaggatct aacagaactc gccgtgaaga ctggcgaaca gttcatacag agtcttttac      540
gactcaatga caagaagaaa atcttcgtca acatggtgga gcacgacact ctcgtctact      600
ccaagaatat caaagataca gtctcagaag accaaagggc tattgagact tttcaacaaa      660
gggtaatatc gggaaacctc ctcggattcc attgcccagc tatctgtcac ttcatcaaaa      720
ggacagtaga aaggaaggt ggcacctaca aatgccatca ttgcgataaa ggaaaggcta       780
tcgttcaaga tgcccctgcc gacagtggtc ccaaagatgg acccccaccc acgaggagca      840
tcgtggaaaa agaagacgtt ccaaccacgt cttcaaagca agtggattga tgtgatatct      900
ccactgacgt aagggatgac gcacaatccc actatccttc gcaagaccct tcctctatat      960
aaggaagttc atttcatttg gagaggactc gagctcattt ctctattact tcagccataa     1020
caaaagaact cttttctctt cttattaaac caggtaacca ccccgcccct ctcctctttc     1080
tttctccgtt ttttttttcc gtctcggtct cgatctttgg ccttggtagt ttgggtgggc     1140
gagaggcggc ttcgtgcgcg cccagatcgg tgcgcgggag gggcgggatc tcgcggctgg     1200
ggctctcgcc ggcgtggatc cggcccggat ctcgcgggga atgggctct cggatgtaga      1260 tctgcgatcc gccgttgttg ggggagatga tgggggggttt aaaatttccg ccatgctaaa     1320
caagatcagg aagaggggaa aagggcacta tggtttatat tttatatat ttctgctgct      1380 tcgtcaggct tagatgtgct agatctttct ttcttctttt tgtgggtaga atttgaatcc     1440
ctcagcattg ttcatcggta gttttcttt tcatgatttg tgacaaatgc agcctcgtgc      1500
ggagcttttt tgtaggtaga ccatggtccg tcctgtagaa accccaaccc gtgaaatcaa     1560
aaaactcgac ggcctgtggg cattcagtct ggatcgcgaa aactgtggaa ttgatcagcg     1620
ttggtgggaa agcgcgttac aagaaagccg ggcaattgct gtgccaggca gttttaacga     1680
tcagttcgcc gatgcagata ttcgtaatta tgcgggcaac gtctggtatc agcgcgaagt     1740
ctttataccg aaaggttggg caggccagcg tatcgtgctg cgtttcgatg cggtcactca     1800
ttacggcaaa gtgtgggtca ataatcagga agtgatggag catcagggcg gctatacgcc     1860
atttgaagcc gatgtcacgc cgtatgttat tgccggaaa agtgtacgta agtttctgct      1920 tctaccttttg atatatatat aataattatc attaattagt agtaatataa tatttcaaat    1980
atttttttca aaataaaaga atgtagtata tagcaattgc ttttctgtag ttataagtg      2040 tgtatatttt aatttataac ttttctaata tatgaccaaa atttgttgat gtgcaggtat     2100
caccgtttgt gtgaacaacg aactgaactg gcagactatc ccgccgggaa tggtgattac     2160
cgacgaaaac ggcaagaaaa agcagtctta cttccatgat ttctttaact atgccggaat     2220
ccatcgcagc gtaatgctct acaccacgcc gaacacctgg gtggacgata tcaccgtggt     2280
gacgcatgtc gcgcaagact gtaaccacgc gtctgttgac tggcaggtgg tggccaatgg     2340
tgatgtcagc gttgaactgc gtgatgcgga tcaacaggtg gttgcaactg acaaggcac      2400 tagcgggact ttgcaagtgg tgaatccgca cctctggcaa ccgggtgaag ttatctcta     2460 tgaactgtgc gtcacagcca aaagccagac agagtgtgat atctacccgc ttcgcgtcgg     2520
catccggtca gtggcagtga agggcgaaca gttcctgatt aaccacaaac cgttctactt     2580
```

```
tactggcttt ggtcgtcatg aagatgcgga cttgcgtggc aaaggattcg ataacgtgct    2640
gatggtgcac gaccacgcat taatggactg gattggggcc aactcctacc gtacctcgca    2700
ttacccttac gctgaagaga tgctcgactg ggcagatgaa catggcatcg tggtgattga    2760
tgaaactgct gctgtcggct ttaacctctc tttaggcatt ggtttcgaag cgggcaacaa    2820
gccgaaagaa ctgtacagcg aagaggcagt caacgggaa actcagcaag cgcacttaca    2880
ggcgattaaa gagctgatag cgcgtgacaa aaaccaccca agcgtggtga tgtggagtat    2940
tgccaacgaa ccggataccc gtccgcaagg tgcacgggaa tatttcgcgc cactggcgga    3000
agcaacgcgt aaactcgacc cgacgcgtcc gatcacctgc gtcaatgtaa tgttctgcga    3060
cgctcacacc gataccatca gcgatctctt tgatgtgctg tgcctgaacc gttattacgg    3120
atggtatgtc caaagcggcg atttggaaac ggcagagaag gtactggaaa aagaacttct    3180
ggcctggcag gagaaactgc atcagccgat tatcatcacc gaatacggcg tggatacgtt    3240
agccgggctg cactcaatgt acaccgacat gtggagtgaa gagtatcagt gtgcatggct    3300
ggatatgtat caccgcgtct ttgatcgcgt cagcgccgtc gtcggtgaac aggtatggaa    3360
tttcgccgat tttgcgacct cgcaaggcat attgcgcgtt ggcggtaaca agaaagggat    3420
cttcactcgc gaccgcaaac cgaagtcggc ggcttttctg ctgcaaaaac gctggactgg    3480
catgaacttc ggtgaaaaac cgcagcaggg aggcaaacaa tgattgctag cacgcgtcgg    3540
gctcaagccc taaactgaac gggatagtca tgctcaaacc agtttctaca cggcaagaat    3600
ttactgattc ttatactttt gcagtcaatt aaattatggt ttttatatat gtaattttgt    3660
atccgattgt agagatcgga agagcgtcgg ccacggaggc cccctagact tgtacatctt    3720
ctggattggc caacttaatt aatgtatgaa ataaaaggat gcacacatag tgacatgcta    3780
atcactataa tgtgggcatc aaagttgtgt gttatgtgta attactaatt atctgaataa    3840
gagaaagaga tcatccatat ttcttatcct aaatgaatgt cacgtgtctt tataattctt    3900
tgatgaacca gatgcatttt attaaccaat tccggcgcgc cagcttggcg taatcatggt    3960
catagctgtt tcctgtgtga aattgttatc cgctcacaat tccacacaac atacgagccg    4020
gaagcataaa gtgtaaagcc tggggtgcct aatgagtgag ctaactcaca ttaattgcgt    4080
tgcgctcact gcccgctttc cagtcgggaa acctgtcgtg ccagctgcat taatgaatcg    4140
gccaacgcgc ggggagaggc ggtttgcgta ttgggcgctc ttccgcttcc tcgctcactg    4200
actcgctgcg ctcggtcgtt cggctgcggc gagcggtatc agctcactca aaggcggtaa    4260
tacggttatc cacagaatca ggggataacg caggaaagaa catgtgagca aaaggccagc    4320
aaaaggccag gaaccgtaaa aaggccgcgt tgctggcgtt tttccatagg ctccgccccc    4380
ctgacgagca tcacaaaaat cgacgctcaa gtcagaggtg gcgaaacccg acaggactat    4440
aaagatacca ggcgtttccc cctggaagct ccctcgtgcg ctctcctgtt ccgaccctgc    4500
cgcttaccgg atacctgtcc gcctttctcc cttcgggaag cgtggcgctt tctcatagct    4560
cacgctgtag gtatctcagt tcggtgtagg tcgttcgctc caagctgggc tgtgtgcacg    4620
aaccccccgt tcagcccgac cgctgcgcct tatccggtaa ctatcgtctt gagtccaacc    4680
cggtaagaca cgacttatcg ccactggcag cagccactgg taacaggatt agcagagcga    4740
ggtatgtagg cggtgctaca gagttcttga agtggtggcc taactacggc tacactagaa    4800
gaacagtatt tggtatctgc gctctgctga agccagttac cttcggaaaa agagttggta    4860
gctcttgatc cggcaaacaa accaccgctg gtagcggtgg ttttttgtt tgcaagcagc    4920
```

```
agattacgcg cagaaaaaaa ggatctcaag aagatccttt gatcttttct acggggtctg    4980
acgctcagtg gaacgaaaac tcacgttaag ggattttggt catgagatta tcaaaaagga    5040
tcttcaccta gatcctttta aattaaaaat gaagttttaa atcaatctaa agtatatatg    5100
agtaaacttg gtctgacagt taccaatgct taatcagtga ggcacctatc tcagcgatct    5160
gtctatttcg ttcatccata gttgcctgac tccccgtcgt gtagataact acgatacggg    5220
agggcttacc atctggcccc agtgctgcaa tgataccgcg agacccacgc tcaccggctc    5280
cagatttatc agcaataaac cagccagccg aagggccga gcgcagaagt ggtcctgcaa    5340
ctttatccgc ctccatccag tctattaatt gttgccggga agctagagta agtagttcgc    5400
cagttaatag tttgcgcaac gttgttgcca ttgctacagg catcgtggtg tcacgctcgt    5460
cgtttggtat ggcttcattc agctccggtt cccaacgatc aaggcgagtt acatgatccc    5520
ccatgttgtg caaaaaagcg gttagctcct tcggtcctcc gatcgttgtc agaagtaagt    5580
tggccgcagt gttatcactc atggttatgg cagcactgca taattctctt actgtcatgc    5640
catccgtaag atgcttttct gtgactggtg agtactcaac caagtcattc tgagaatagt    5700
gtatgcggcg accgagttgc tcttgcccgg cgtcaatacg ggataatacc gcgccacata    5760
gcagaacttt aaaagtgctc atcattggaa acgttcttc ggggcgaaaa ctctcaagga    5820
tcttaccgct gttgagatcc agttcgatgt aacccactcg tgcacccaac tgatcttcag    5880
catcttttac tttcaccagc gtttctgggt gagcaaaaac aggaaggcaa aatgccgcaa    5940
aaaagggaat aagggcgaca cggaaatgtt gaatactcat actcttcctt tttcaatatt    6000
attgaagcat ttatcagggt tattgtctca tgagcggata catatttgaa tgtatttaga    6060
aaaataaaca ataggggtt ccgcgcacat ttccccgaaa agtgccacct gacgtctaag    6120
aaaccattat tatcatgaca ttaacctata aaaataggcg tatcacgagg ccctttcgtc    6180
```

<210> SEQ ID NO 12
<211> LENGTH: 5591
<212> TYPE: DNA
<213> ORGANISM: Artificial Sequence
<220> FEATURE:
<223> OTHER INFORMATION: vector

<400> SEQUENCE: 12

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt gggcccggcc ggccgcgatc     420
gctacgtacc tgcaggcccg ggttaattaa gcggccgcag gctaactggg cccttaaggg     480
taccgaaggc cagacgggca cactgaatca tggccgcaag acccttcctc tatataagga     540
agttcatttc atttggagag gactcgagct catttctcta ttacttcagc cataacaaaa     600
gaactctttt ctcttcttat taaaccaggt aaccacccc cccctctcct ctttctttct     660
ccgttttttt tttccgtctc ggtctcgatc tttggccttg gtagtttggg tgggcgagag    720
gcggcttcgt gcgcgcccag atcggtgcgc gggaggggcg ggatctcgcg ctgggctc     780 tcgccggcgt ggatccggcc cggatctcgc ggggaatggg gctctcggat gtagatctgc     840
```

-continued

```
gatccgccgt tgttggggga gatgatgggg ggtttaaaat ttccgccatg ctaaacaaga    900
tcaggaagag gggaaaaggg cactatggtt tatattttta tatatttctg ctgcttcgtc    960
aggcttagat gtgctagatc tttctttctt cttttgtgg gtagaatttg aatccctcag    1020
cattgttcat cggtagtttt tcttttcatg atttgtgaca aatgcagcct cgtgcggagc    1080
ttttttgtag gtagaccatg gtccgtcctg tagaaacccc aacccgtgaa atcaaaaaac    1140
tcgacggcct gtgggcattc agtctggatc gcgaaaactg tggaattgat cagcgttggt    1200
gggaaagcgc gttacaagaa agccgggcaa ttgctgtgcc aggcagtttt aacgatcagt    1260
tcgccgatgc agatattcgt aattatgcgg gcaacgtctg gtatcagcgc gaagtcttta    1320
taccgaaagg ttgggcaggc cagcgtatcg tgctgcgttt cgatgcggtc actcattacg    1380
gcaaagtgtg ggtcaataat caggaagtga tggagcatca gggcggctat acgccatttg    1440
aagccgatgt cacgccgtat gttattgccg ggaaaagtgt acgtaagttt ctgcttctac    1500
ctttgatata tatataataa ttatcattaa ttagtagtaa tataatattt caaatatttt    1560
tttcaaaata aagaatgta gtatatagca attgcttttc tgtagtttat aagtgtgtat    1620
atttttaattt ataacttttc taatatatga ccaaaatttg ttgatgtgca ggtatcaccg    1680
tttgtgtgaa caacgaactg aactggcaga ctatcccgcc gggaatggtg attaccgacg    1740
aaaacggcaa gaaaaagcag tcttacttcc atgatttctt taactatgcc ggaatccatc    1800
gcagcgtaat gctctacacc acgccgaaca cctgggtgga cgatatcacc gtggtgacgc    1860
atgtcgcgca agactgtaac cacgcgtctg ttgactggca ggtggtggcc aatggtgatg    1920
tcagcgttga actgcgtgat gcggatcaac aggtggttgc aactggacaa ggcactagcg    1980
ggactttgca agtggtgaat ccgcaccctct ggcaaccggg tgaaggttat ctctatgaac    2040
tgtgcgtcac agccaaaagc cagacagagt gtgatatcta cccgcttcgc gtcggcatcc    2100
ggtcagtggc agtgaagggc gaacagttcc tgattaacca caaaccgttc tactttactg    2160
gctttggtcg tcatgaagat gcggacttgc gtggcaaagg attcgataac gtgctgatgg    2220
tgcacgacca cgcattaatg gactggattg gggccaactc ctaccgtacc tcgcattacc    2280
cttacgctga agagatgctc gactgggcag atgaacatgg catcgtggtg attgatgaaa    2340
ctgctgctgt cggctttaac ctctctttag gcattggttt cgaagcgggc aacaagccga    2400
aagaactgta cagcgaagag gcagtcaacg gggaaactca gcaagcgcac ttacaggcga    2460
ttaaagagct gatagcgcgt gacaaaaacc acccaagcgt ggtgatgtgg agtattgcca    2520
acgaaccgga tacccgtccg caaggtgcac gggaatattt cgcgccactg gcggaagcaa    2580
cgcgtaaact cgacccgacg cgtccgatca cctgcgtcaa tgtaatgttc tgcgacgctc    2640
acaccgatac catcagcgat ctctttgatg tgctgtgcct gaaccgttat tacggatggt    2700
atgtccaaag cggcgatttg gaaacggcag agaaggtact ggaaaaagaa cttctggcct    2760
ggcaggagaa actgcatcag ccgattatca tcaccgaata cggcgtggat acgttagccg    2820
ggctgcactc aatgtacacc gacatgtgga gtgaagagta tcagtgtgca ggctggata    2880
tgtatcaccg cgtctttgat cgcgtcagcg ccgtcgtcgg tgaacaggta tggaatttcg    2940
ccgattttgc gacctcgcaa ggcatattgc gcgttggcgg taacaagaaa gggatcttca    3000
ctcgcgaccg caaaccgaag tcggcggctt ttctgctgca aaaacgctgg actggcatga    3060
acttcggtga aaaccgcag cagggaggca acaatgatt gctagcacgc gtccctagac    3120
ttgtacatct tctggattgg ccaacttaat taatgtatga aataaaagga tgcacacata    3180
```

```
gtgacatgct aatcactata atgtgggcat caaagttgtg tgttatgtgt aattactaat   3240
tatctgaata agagaaagag atcatccata tttcttatcc taaatgaatg tcacgtgtct   3300
ttataattct tgatgaacc agatgcattt tattaaccaa ttccggcgcg ccagcttggc    3360
gtaatcatgg tcatagctgt ttcctgtgtg aaattgttat ccgctcacaa ttccacacaa   3420
catacgagcc ggaagcataa agtgtaaagc ctggggtgcc taatgagtga gctaactcac   3480
attaattgcg ttgcgctcac tgcccgcttt ccagtcggga acctgtcgt gccagctgca    3540 ttaatgaatc ggccaacgcg cggggagagg cggtttgcgt attgggcgct cttccgcttc   3600
ctcgctcact gactcgctgc gctcggtcgt tcggctgcgg cgagcggtat cagctcactc   3660
aaaggcggta atacggttat ccacagaatc agggggataac gcaggaaaga acatgtgagc   3720
aaaaggccag caaaaggcca ggaaccgtaa aaaggccgcg ttgctggcgt ttttccatag   3780
gctccgcccc cctgacgagc atcacaaaaa tcgacgctca agtcagaggt ggcgaaaccc   3840
gacaggacta taaagatacc aggcgtttcc ccctggaagc tccctcgtgc gctctcctgt   3900
tccgaccctg ccgcttaccg gatacctgtc cgcctttctc ccttcgggaa gcgtggcgct   3960
ttctcatagc tcacgctgta ggtatctcag ttcggtgtag tcgttcgct ccaagctggg    4020 ctgtgtgcac gaacccccg ttcagcccga ccgctgcgcc ttatccggta actatcgtct    4080
tgagtccaac ccggtaagac acgacttatc gccactggca gcagccactg gtaacaggat   4140
tagcagagcg aggtatgtag gcggtgctac agagttcttg aagtggtggc ctaactacgg   4200
ctacactaga agaacagtat ttggtatctg cgctctgctg aagccagtta ccttcggaaa   4260
aagagttggt agctcttgat ccggcaaaca aaccaccgct ggtagcggtg gttttttgt    4320 ttgcaagcag cagattacgc gcagaaaaaa aggatctcaa aagatccctt gatcttttc    4380 tacgggtct gacgctcagt ggaacgaaaa ctcacgttaa gggattttgg tcatgagatt    4440 atcaaaagg atcttcacct agatcctttt aaattaaaaa tgaagtttta aatcaatcta    4500
aagtatatat gagtaaactt ggtctgacag ttaccaatgc ttaatcagtg aggcaccctat   4560 ctcagcgatc tgtctatttc gttcatccat agttgcctga ctccccgtcg tgtagataac   4620
tacgatacgg gagggcttac catctggccc cagtgctgca atgataccgc gagacccacg   4680
ctcaccggct ccagatttat cagcaataaa ccagccagcc ggaagggccg agcgcagaag   4740
tggtcctgca actttatccg cctccatcca gtctattaat tgttgccggg aagctagagt   4800
aagtagttcg ccagttaata gtttgcgcaa cgttgttgcc attgctacag gcatcgtggt   4860
gtcacgctcg tcgtttggta tggcttcatt cagctccggt tcccaacgat caaggcgagt   4920
tacatgatcc cccatgttgt gcaaaaaagc ggttagctcc ttcggtcctc cgatcgttgt   4980
cagaagtaag ttggccgcag tgttatcact catggttatg gcagcactgc ataattctct   5040
tactgtcatg ccatccgtaa gatgcttttc tgtgactggt gagtactcaa ccaagtcatt   5100
ctgagaatag tgtatgcggc gaccgagttg ctcttgcccg gcgtcaatac gggataatac   5160
cgcgccacat agcagaactt taaaagtgct catcattgga aaacgttctt cggggcgaaa   5220
actctcaagg atcttaccgc tgttgagatc cagttcgatg taacccactc gtgcacccaa   5280
ctgatcttca gcatctttta ctttcaccag cgtttctggg tgagcaaaaa caggaaggca   5340
aaatgccgca aaaaagggaa taagggcgac acggaaatgt tgaatactca tactcttcct   5400
ttttcaatat tattgaagca tttatcaggg ttattgtctc atgagcggat acatatttga   5460
atgtatttag aaaaataaac aaataggggt tccgcgcaca tttccccgaa aagtgccacc   5520
tgacgtctaa gaaaccatta ttatcatgac attaacctat aaaaataggc gtatcacgag   5580
```

<210> SEQ ID NO 13
<211> LENGTH: 58
<212> TYPE: DNA
<213> ORGANISM: Artificial Sequence
<220> FEATURE:
<223> OTHER INFORMATION: primer

<400> SEQUENCE: 13

```
aatgatacgg cgaccaccga gatctacact ctttccctac acgacgctct tccgatct          58
```

<210> SEQ ID NO 14
<211> LENGTH: 84
<212> TYPE: DNA
<213> ORGANISM: Artificial Sequence
<220> FEATURE:
<223> OTHER INFORMATION: primer

<400> SEQUENCE: 14

```
caagcagaag acggcatacg agatattggc gtgactggag ttcagacgtg tgctcttccg        60
atctaagagt atcagtgtgc atgg                                              84
```

<210> SEQ ID NO 15
<211> LENGTH: 6439
<212> TYPE: DNA
<213> ORGANISM: Artificial Sequence
<220> FEATURE:
<223> OTHER INFORMATION: vector

<400> SEQUENCE: 15

```
ctgcagtgca gcgtgacccg gtcgtgcccc tctctagaga taatgagcat tgcatgtcta        60
agttataaaa aattaccaca tattttttt gtcacacttg tttgaagtgc agtttatcta       120
tctttataca tatatttaaa ctttactcta cgaataatat aatctatagt actacaataa      180
tatcagtgtt ttagagaatc atataaatga acagttagac atggtctaaa ggacaattga      240
gtattttgac aacaggactc tacagtttta tcttttagt gtgcatgtgt tctccttttt      300
ttttgcaaat agcttcacct atataatact tcatccattt tattagtaca tccatttagg      360
gtttagggtt aatggttttt atagactaat ttttttagta catctatttt attctatttt      420
agcctctaaa ttaagaaaac taaaactcta ttttagtttt tttatttaat aatttagata      480
taaaatagaa taaaataaag tgactaaaaa ttaaacaaat acctttaag aaattaaaaa        540 aactaaggaa acatttttct tgtttcgagt agataatgcc agcctgttaa acgccgtcga      600
tcgacgagtc taacggacac caaccagcga accagcagcg tcgcgtcggg ccaagcgaag      660
cagacggcac ggcatctctg tcgctgcctc tggacccctc tcgagagttc cgctccaccg      720
ttggacttgc tccgctgtcg gcatccagaa attgcgtggc ggagcggcag acgtgagccg      780
gcacggcagg cggcctcctc ctcctctcac ggcaccggca gctacggggg attccttttcc    840 caccgctcct tcgctttccc ttcctcgccc gccgtaataa atagacaccc cctccacacc      900
ctctttcccc aacctcgtgt tgttcggagc gcacacacac acaaccagat ctcccccaaa      960
tccacccgtc ggcacctccg cttcaaggta cgccgctcgt cctccccccc cccccctctc     1020
taccttctct agatcggcgt tccggtccat gcttagggcc cggtagttct acttctgtcc     1080
atgtttgtgt tagatccgtg tttgtgttag atccgtgcta ctagcgttcg tacacggatg     1140
cgacctgtac gtcagacacg ttctgattgc taacttgcca gtgtttctct ttggggaatc     1200
```

-continued

```
ctgggatggc tctagccgtt ccgcagacgg gatcgatttc atgatttttt ttgtttcgtt    1260
gcatagggtt tggtttgccc ttttcctttg tttcaatata tgccgtgcac ttgtttgtcg    1320
ggtcatcttt tcatgctttt ttttgtcttg gttgtgatga tgtggtctgg ttgggcggtc    1380
gttctagatc ggagtagaat tctgtttcaa actacctggt ggatttatta attttggatc    1440
tgtatgtgtg tgccatacat attcatagtt acgaattgaa gatgatggat ggaaatatcg    1500
atctaggata ggtatacatg ttgatgcggg ttttactgat gcatacacag agatgctttt    1560
tgttcgcttg gttgtgatga tgtggtgtgg ttgggcggtc gttcattcgt tctagatcgg    1620
agtagaatac tgtttcaaac tacctggtgt atttattaat tttggaactg tatgtgtgtg    1680
tcatacatct tcatagttac gagtttaaga tggatggaaa tatcgatcta ggataggtat    1740
acatgttgat gtgggtttta ctgatgcata tacatgatgg catatgcagc atctattcat    1800
atgctctaac cttgagtacc tatctattat aataaacaag tatgttttat aattattttg    1860
atcttgatat acttggatga tggcatatgc agcagctata tgtggatttt tttagccctg    1920
ccttcatacg ctatttattt gcttggtact gtttcttttg tcgatgctca ccctgttgtt    1980
tggtgttact tctgcaggtc gaccgccggg gatcaccaaa accatggaag acgccaaaaa    2040
cataaagaaa ggcccggcgc cattctatcc gctggaagat ggaaccgctg gagagcaact    2100
gcataaggct atgaagagat acgccctggt tcctggaaca attgctttta cagatgcaca    2160
tatcgaggtg gacatcactt acgctgagta cttcgaaatg tccgttcggt tggcagaagc    2220
tatgaaacga tatgggctga atacaaatca cagaatcgtc gtatgcagtg aaaactctct    2280
tcaattcttt atgccggtgt tgggcgcgtt atttatcgga gttgcagttg cgcccgcgaa    2340
cgacatttat aatgaacgtg aattgctcaa cagtatgggc atttcgcagc ctaccgtggt    2400 gttcgttttcc aaaaggggt tgcaaaaaat tttgaacgtg caaaaaaagc tcccaatcat    2460
ccaaaaaatt attatcatgg attctaaaac ggattaccag ggatttcagt cgatgtacac    2520
gttcgtcaca tctcatctac ctcccggttt taatgaatac gattttgtgc cagagtcctt    2580
cgatagggac aagacaattg cactgatcat gaactcctct ggatctactg gtctgcctaa    2640
aggtgtcgct ctgcctcata gaactgcctg cgtgagattc tcgcatgcca gagatcctat    2700
ttttggcaat caaatcattc cggatactgc gattttaagt gttgttccat tccatcacgg    2760
ttttggaatg tttactacac tcggatattt gatatgtgga tttcgagtcg tcttaatgta    2820
tagatttgaa gaagagctgt ttctgaggag ccttcaggat tacaagattc aaagtgcgct    2880
gctggtgcca acccctattct ccttcttcgc caaaagcact ctgattgaca atacgatttt    2940
atctaattta cacgaaattg cttctggtgg cgctcccctc tctaaggaag tcggggaagc    3000
ggttgccaag aggttccatc tgccaggtat caggcaagga tatgggctca ctgagactac    3060
atcagctatt ctgattacac ccgaggggga tgataaaccg ggcgcggtcg gtaaagttgt    3120 tccattttttt gaagcgaagg ttgtggatct ggataccggg aaaacgctgg gcgttaatca    3180
aagaggcgaa ctgtgtgtga aggtccctat gattatgtcc ggttatgtaa acaatccgga    3240
agcgaccaac gccttgattg acaaggatgg atggctacat tctggagaca tagcttactg    3300
ggacgaagac gaacacttct tcatcgttga ccgcctgaag tctctgatta agtacaaagg    3360
ctatcaggtg gctcccgctg aattggaatc catcttgctc caacacccca acatcttcga    3420
cgcaggtgtc gcaggtcttc ccgacgatga cgccggtgaa cttcccgccg ccgttgttgt    3480
tttggagcac ggaaagacga tgacggaaaa agagatcgtg gattacgtcg ccagtcaagt    3540
aacaaccgcg aaaaagttgc gcggaggagt tgtgtttgtg gacgaagtac cgaaaggtct    3600
```

```
taccggaaaa ctcgacgcaa gaaaaatcag agagatcctc ataaaggcca agaagggcgg   3660
aaagatcgcc gtgtaattct agcaagcttg gacacgctga atcaccagt ctctctctac    3720 aaatctatct ctctctattt tctccataat aatgtgtgag tagttcccag ataagggaat   3780
tagggttcct atagggtttc gctcatgtgt tgagcatata agaaacccctt agtatgtatt  3840 tgtatttgta aaatacttct atcaataaaa tttctaattc ctaaaaccaa atccagtac    3900 taaaatccag atcatgcatg gtacagcggc cgcgttaacg cgtatactct agagcgatcg   3960
caagcttggc gtaatcatgg tcatagctgt ttcctgtgtg aaattgttat ccgctcacaa   4020
ttccacacaa catacgagcc ggaagcataa agtgtaaagc ctggggtgcc taatgagtga   4080
gctaactcac attaattgcg ttgcgctcac tgcccgcttt ccagtcggga acctgtcgt    4140 gccagctgca ttaatgaatc ggccaacgcg cggggagagg cggtttgcgt attgggcgct   4200
cttccgcttc ctcgctcact gactcgctgc gctcggtcgt tcggctgcgg cgagcggtat   4260
cagctcactc aaaggcggta atacggttat ccacagaatc aggggataac gcaggaaaga   4320
acatgtgagc aaaaggccag caaaaggcca ggaaccgtaa aaaggccgcg ttgctggcgt   4380
ttttccatag gctccgcccc cctgacgagc atcacaaaaa tcgacgctca agtcagaggt   4440
ggcgaaaccc gacaggacta taaagatacc aggcgtttcc ccctggaagc tccctcgtgc   4500
gctctcctgt tccgaccctg ccgcttaccg gatacctgtc cgcctttctc ccttcgggaa   4560
gcgtggcgct ttctcaaagc tcacgctgta ggtatctcag ttcggtgtag tcgttcgct    4620 ccaagctggg ctgtgtgcac gaaccccccg ttcagcccga ccgctgcgcc ttatccggta   4680
actatcgtct tgagtccaac ccggtaagac acgacttatc gccactggca gcagccactg   4740
gtaacaggat tagcagagcg aggtatgtag gcggtgctac agagttcttg aagtggtggc   4800
ctaactacgg ctacactaga agaacagtat ttggtatctg cgctctgctg aagccagtta   4860
ccttcggaaa aagagttggt agctcttgat ccggcaaaca aaccaccgct ggtagcggtg   4920
gtttttttgt ttgcaagcag cagattacgc gcagaaaaaa aggatctcaa gaagatcctt   4980
tgatcttttc tacggggtct gacgctcagt ggaacgaaaa ctcacgttaa gggattttgg   5040
tcatgagatt atcaaaaagg atcttcacct agatcctttt aaattaaaaa tgaagtttta   5100
aatcaatcta agtatatat gagtaaactt ggtctgacag ttaccaatgc ttaatcagtg    5160
aggcacctat ctcagcgatc tgtctatttc gttcatccat agttgcctga ctccccgtcg   5220
tgtagataac tacgatacgg gagggcttac catctggccc cagtgctgca atgataccgc   5280
gagacccacg ctcaccggct ccagatttat cagcaataaa ccagccagcc ggaagggccg   5340
agcgcagaag tggtcctgca actttatccg cctccatcca gtctattaat gttgccggg    5400 aagctagagt aagtagttcg ccagttaata gtttgcgcaa cgttgttgcc attgctacag   5460
gcatcgtggt gtcacgctcg tcgtttggta tggcttcatt cagctccggt tcccaacgat   5520
caaggcgagt tacatgatcc cccatgttgt gcaaaaaagc ggttagctcc ttcggtcctc   5580
cgatcgttgt cagaagtaag ttggccgcag tgttatcact catggttatg gcagcactgc   5640
ataattctct tactgtcatg ccatccgtaa gatgcttttc tgtgactggt gagtactcaa   5700
ccaagtcatt ctgagaatag tgtatgcggc gaccgagttg ctcttgcccg gcgtcaatac   5760
gggataatac cgcgccacat agcagaactt taaaagtgct catcattgga aaacgttctt   5820
cggggcgaaa actctcaagg atcttaccgc tgttgagatc cagttcgatg taacccactc   5880
gtgcacccaa ctgatcttca gcatctttta ctttcaccag cgtttctggg tgagcaaaaa   5940
```

| | |
|---|---|
| caggaaggca aaatgccgca aaaaagggaa taagggcgac acggaaatgt tgaatactca | 6000 |
| tactcttcct ttttcaatat tattgaagca tttatcaggg ttattgtctc atgagcggat | 6060 |
| acatatttga atgtatttag aaaaataaac aataggggt tccgcgcaca tttccccgaa | 6120 |
| aagtgccacc tgacgtctaa gaaccatta ttatcatgac attaacctat aaaaataggc | 6180 |
| gtatcacgag gcccttcgt ctcgcgcgtt tcggtgatga cggtgaaaac ctctgacaca | 6240 |
| tgcagctccc ggagacggtc acagcttgtc tgtaagcgga tgccgggagc agacaagccc | 6300 |
| gtcagggcgc gtcagcgggt gttggcgggt gtcggggctg gcttaactat gcggcatcag | 6360 |
| agcagattgt actgagagtg caccatacct gcaggcaatt ggtacctacg tatgcatggc | 6420 |
| gcgccataag cttgcatgc | 6439 |

<210> SEQ ID NO 16
<211> LENGTH: 144
<212> TYPE: DNA
<213> ORGANISM: Triticum aestivum

<400> SEQUENCE: 16

| | |
|---|---|
| gaattggtga gtgggtgaag ggaggcaaga cttgacccag agcacgcatc tacgtggact | 60 |
| cctcggtggg tccatccgtc atcacgccca catggcgtcc tcccattggc cacaaccccg | 120 |
| cccgggagcc tctgattggc cgga | 144 |

<210> SEQ ID NO 17
<211> LENGTH: 144
<212> TYPE: DNA
<213> ORGANISM: Triticum aestivum

<400> SEQUENCE: 17

| | |
|---|---|
| cgattttctt ttaggaagaa aatggtatgg agattccaaa ttctcctctc ctttcctttt | 60 |
| gcgcaagaaa gaaagaagat gggggggcgg agagaatggc cgagttgtga aatctaaaca | 120 |
| cgaagggtca aataatacgg ggta | 144 |

<210> SEQ ID NO 18
<211> LENGTH: 144
<212> TYPE: DNA
<213> ORGANISM: Triticum aestivum

<400> SEQUENCE: 18

| | |
|---|---|
| atgcgccatg tcgccgtcac gtaccgctca tgggtttcgt gcccggccca gtttcgcaac | 60 |
| gctcgcttgc gacacgcact atgtgacctc agccactcca tccggatatg gacacccgct | 120 |
| tttttcctca cctgccctcg gaag | 144 |

<210> SEQ ID NO 19
<211> LENGTH: 144
<212> TYPE: DNA
<213> ORGANISM: Triticum aestivum

<400> SEQUENCE: 19

| | |
|---|---|
| atgtatgcag ccgtctcctg ctgcttcact caaggacgcc acgccatcca cgcatatccg | 60 |
| gtggcggcaa acgccgtcca ggttcaacga acgccgttcc ccccggtcca ccagcgccag | 120 |
| ccgcctccgg ccgggcccac ccgc | 144 |

<210> SEQ ID NO 20
<211> LENGTH: 144
<212> TYPE: DNA
<213> ORGANISM: Triticum aestivum

<400> SEQUENCE: 20

```
tagactcggt tgcttttcat aaaactaact ttgtattttc ctctaagatg ataagatgaa    60
atgacgcctg tagagcatga catgactcat tgaattccct ttacacgtaa aggatggtaa   120
ttgcttacaa gctactccta ctag                                         144
```

<210> SEQ ID NO 21
<211> LENGTH: 144
<212> TYPE: DNA
<213> ORGANISM: Triticum aestivum

<400> SEQUENCE: 21

```
aaaactaact ttgtattttc ctctaagatg ataagatgaa atgacgcctg tagagcatga    60
catgactcat tgaattccct ttacacgtaa aggatggtaa ttgcttacaa gctactccta   120
ctagcatata tccggtccta actc                                         144
```

<210> SEQ ID NO 22
<211> LENGTH: 1000
<212> TYPE: DNA
<213> ORGANISM: Triticum aestivum

<400> SEQUENCE: 22

```
gttgcggcgg acaccggtca tagattctgg atcccttacc gcggggcaaa aggggccgcc    60
actcacgatt cacacgcatg ggggaatgcg gtttggaggc tggttgttgt gttccaacac   120
gtcgtctgtt gcaacggtca agttggggga ggaggctgcg cgtggtccag cttgcggcaa   180
atcggacgac tccgcagcac ctgatctaac tgctcgcatg agagcttact tttggcatgc   240
atcacagcca cgataaaaca aggctaacat agtcttggtc catctataat acatgttgga   300
ccatgcttct ctctccccac taatcgattg cttctctcctt tgaccgtatt tgatcttatt   360
ttttcttcta gtattttatt ttctcttgac attgggttta ttggatgtgc gcggctcccg   420
catgtcagtg accaacatca aggacactc cttccgccaa agtccctctg attcttcgag   480
tcgattttcc cccttgcaac agatggctat atgtgactga tcgagaaatg gccacacatt   540
tcatccaaaa atgaagaata tttgaatttc cacagcctcc agagcaccac tttgatttga   600
actcgaaata tgaatatagt aaaagggtct acatataatt tgaaagtatt ttgcaggaca   660
aaaacaacaa tgttattctc gaatcttaat ctatagtcgt caattaaatt ttcagaatgt   720
taactgttca tataattgtg caccctgcaa ttgtgaatga aaaacgaca catgtccact   780
ccggttagaa aaacgcagt agttccacta gtatgggtac cgacccaacg ccgctccgcc   840
tttataagta ccgacacttc gccattggct tcttcaccca gggaaaaccg gtctggtcgc   900
ctcttcctcg tgaactattc cccactgtca ctgctgggca ccactctcac gcagcgggag   960
gcgcgtgtcg tgagcacacg tgtggttgtt tgcgtgcgcc                        1000
```

<210> SEQ ID NO 23
<211> LENGTH: 16
<212> TYPE: DNA
<213> ORGANISM: Triticum aestivum

<400> SEQUENCE: 23

```
caggttcaac gaacgc                                                   16
```

<210> SEQ ID NO 24
<211> LENGTH: 21
<212> TYPE: DNA

```
<213> ORGANISM: Triticum aestivum

<400> SEQUENCE: 24
gtccaccagc gccagccgcc t                                                     21
```